US009164109B2

(12) United States Patent
Kleinfeld et al.

(10) Patent No.: US 9,164,109 B2
(45) Date of Patent: Oct. 20, 2015

(54) USE OF PROBES FOR UNBOUND METABOLITES

(75) Inventors: Alan Marc Kleinfeld, La Jolla, CA (US); Andrew Henry Huber, Encinitas, CA (US); James Patrick Kampf, San Diego, CA (US); Thomas Kwan, San Diego, CA (US); Baolong Zhu, San Diego, CA (US)

(73) Assignee: Alan Kleinfeld, La Jolla, CA (US)

( * ) Notice: Subject to any disclaimer, the term of this patent is extended or adjusted under 35 U.S.C. 154(b) by 1416 days.

(21) Appl. No.: 12/447,400

(22) PCT Filed: Oct. 26, 2007

(86) PCT No.: PCT/US2007/082725
§ 371 (c)(1),
(2), (4) Date: Apr. 27, 2009

(87) PCT Pub. No.: WO2008/060841
PCT Pub. Date: May 22, 2008

(65) Prior Publication Data
US 2010/0062948 A1    Mar. 11, 2010

Related U.S. Application Data

(60) Provisional application No. 60/854,879, filed on Oct. 27, 2006, provisional application No. 60/899,231, filed on Feb. 2, 2007, provisional application No. 60/958,344, filed on Jul. 5, 2007.

(51) Int. Cl.
*G01N 33/50*     (2006.01)
*G01N 33/92*     (2006.01)
*G01N 33/72*     (2006.01)

(52) U.S. Cl.
CPC .............. *G01N 33/92* (2013.01); *G01N 33/728* (2013.01)

(58) Field of Classification Search
None
See application file for complete search history.

(56) References Cited

U.S. PATENT DOCUMENTS

| 4,071,413 | A |   | 1/1978  | Takahashi et al. |
|-----------|---|---|---------|------------------|
| 4,369,250 | A |   | 1/1983  | Gindler |
| 4,491,631 | A |   | 1/1985  | Imamura et al. |
| 4,580,059 | A |   | 4/1986  | Wolfbeis et al. |
| 4,833,332 | A |   | 5/1989  | Robertson et al. |
| 5,225,329 | A |   | 7/1993  | Marks |
| 5,227,307 | A |   | 7/1993  | Bar-Or et al. |
| 5,449,607 | A |   | 9/1995  | Wilton |
| 5,470,714 | A | * | 11/1995 | Kleinfeld ...................... 435/7.8 |
| 5,496,735 | A |   | 3/1996  | Schwertner |
| 5,512,429 | A |   | 4/1996  | Wilton |
| 5,604,105 | A |   | 2/1997  | Jackowski |
| 5,914,112 | A |   | 6/1999  | Bednar et al. |
| 5,977,174 | A |   | 11/1999 | Bradley et al. |
| 6,210,976 | B1|   | 4/2001  | Sabbadini |
| 6,264,960 | B1|   | 7/2001  | Robins et al. |
| 6,444,432 | B1| * | 9/2002  | Kleinfeld ...................... 435/7.8 |
| 6,461,875 | B1|   | 10/2002 | Bar-Or et al. |
| 6,475,743 | B1|   | 11/2002 | Bar-Or et al. |
| 6,492,179 | B1|   | 12/2002 | Bar-Or et al. |
| 6,563,585 | B1|   | 5/2003  | Rao et al. |
| 6,727,258 | B2|   | 4/2004  | Baraldi |
| 6,750,030 | B2|   | 6/2004  | Kleinfeld |
| 7,202,089 | B2|   | 4/2007  | Kleinfeld et al. |
| 7,262,017 | B2|   | 8/2007  | Kleinfeld |
| 7,601,510 | B2|   | 10/2009 | Kleinfeld et al. |
| 7,879,558 | B2|   | 2/2011  | Kleinfeld |
| 2002/0142347 | A1| * | 10/2002 | Knudsen et al. ............... 435/7.1 |
| 2002/0168692 | A1|   | 11/2002 | Cass et al. |
| 2002/0182197 | A1|   | 12/2002 | Black et al. |
| 2004/0019109 | A1|   | 1/2004  | Owman et al. |
| 2004/0077017 | A1|   | 4/2004  | Karlstrom et al. |
| 2005/0004485 | A1| * | 1/2005  | Crosby et al. ................. 600/513 |
| 2005/0239155 | A1|   | 10/2005 | Alarcon et al. |
| 2005/0244864 | A1|   | 11/2005 | Kleinfeld et al. |
| 2006/0019235 | A1| * | 1/2006  | Soen et al. ........................ 435/4 |
| 2006/0257938 | A1|   | 11/2006 | Kleinfeld et al. |
| 2007/0166707 | A1| * | 7/2007  | Schadt et al. .................... 435/6 |

FOREIGN PATENT DOCUMENTS

EP    1 043 587 B1    6/2003
SU        1270706    9/1981
(Continued)

OTHER PUBLICATIONS

Yuvienco et al. (Umbilical Cord Unbound Free Fatty Acid Concentration and Low Apgar Score, 2005, American Journal Of Perinatology, vol. 22, No. 8, pp. 429-436).*
Chattopadhyay, et al. "Measurement of Microsecond Dynamic Motion in the Intestinal Fatty Acid Binding Protein by Using Fluorescence Correlation Spectroscopy," *Proceedings of the National Academy of Sciences of the United States of America*, vol. 99, No. 22, pp. 14171-14176, Oct. 29, 2002.
Donato, et al. "A Fluorescence-based Method for Analyzing Retinoic Acid in Biological Samples," *Analytical Biochemistry*, vol. 357, No. 2, pp. 249-256, Oct. 15, 2006.
Supplementary European Search Report issued Dec. 20, 2010 to European patent application No. 09 70 1867.
Davies, et al. "Perioperative Variability of Binding of Lidocaine, Quinidine, and Propranolol After Cardiac Operations," *Journal of Thoracic and Cardiovascular Surgery*, vol. 96, No. 4, pp. 634-641, Oct., 1998.
Ford, et al. "Use of Serum Markers of Myocardial Injury for the Early Diagnosis of Acute Myocardial Infarction,"*ACC Current Journal Review*, vol. 5, No. 3, pp. 86-89, May/Jun., 1996.

(Continued)

*Primary Examiner* — Jason Sims
(74) *Attorney, Agent, or Firm* — Knobbe, Martens, Olson & Bear, LLP

(57) ABSTRACT

Methods of determining levels of unbound metabolites are disclosed. Probes derived from fatty acid binding protein muteins are described that bind preferentially to a number of unbound metabolites including oleate, stearate, linoleate, palmitate, arachidonate and unconjugated bilirubin. A profile for a patient is determined using one or more of the described probes. The profile is useful in diagnosis of disease, particularly myocardial infarction, non-alcoholic fatty liver disease (NAFLD), diabetes, stroke, sepsis and neonatal jaundice. The responses of multiple probes to a test sample are used to classify the degree of acute coronary syndrome by comparison to multi-probe profiles generated from unstable angina, non ST elevation myocardial infarction, and ST elevation myocardial infarction.

20 Claims, 9 Drawing Sheets

(56) References Cited

FOREIGN PATENT DOCUMENTS

| WO | WO 91/09310 | 6/1991 |
|---|---|---|
| WO | WO 93/08276 | 4/1993 |
| WO | WO 94/06014 | 3/1994 |
| WO | WO 98/57171 | 12/1998 |
| WO | WO 00/20840 | 4/2000 |
| WO | WO 00/47734 | 8/2000 |
| WO | WO 00/74728 | 12/2000 |
| WO | WO 02/089656 | 11/2002 |
| WO | WO 2003/093438 | 11/2003 |
| WO | WO 2005/093103 | 10/2005 |

OTHER PUBLICATIONS

Kleinfeld, et al. "Increases in Serum Unbound Free Fatty Acid Levels Following Coronary Angioplasty," *American Journal of Cardiology*, vol. 78, No. 12, pp. 1350-1354, Dec. 15, 1996.

Glatz, et al. "Fatty-Acid-Binding Protein as a Plasma Marker for the Estimation of Myocardial Infarct Size in Humans," *BR Heart J*, vol. 71, pp. 135-140, 1994.

Patel, et al. "Serum Levels of Unbound Free Fatty Acids I: Normative Data in Term Newborn Infants," *Journal of American College of Nutrition*, vol. 16, No. 1, pp. 81-84, 1997.

Peuhkurinen, et al. "Changes in Myocardial Energy Metabolism in Elective Coronary Angioplasty," *Cardiovascular Research*, vol. 25, pp. 158-163, 1991.

Richieri, et al. "Equilibrium Constants for the Binding of Fatty Acids with Fatty Acid-Binding Proteins from Adipocyte, Intestine, Heart, and Liver Measured with the Fluorescent Probe ADIFAB," *The Journal of Biological Chemistry*, vol. 269, No. 39, pp. 23918-23930, Sep. 30, 1994.

Richieri, et al. "Thermodynamic and Kinetic Properties of Fatty Acid Interactions with Rat Liver Fatty Acid-Binding Protein," *The Journal of Biological Chemistry*, vol. 271, No. 49, pp. 31068-31074, Dec. 6, 1996.

Richieri, et al. "Unbound Free Fatty Acid Levels in Human Serum," *Journal of Lipid Research*, vol. 36, No. 2, pp. 229-240, Feb., 1995.

Richieri, et al. "A Fluorescently Labeled Intestinal Fatty Acid Binding Protein. Interactions with Fatty Acids and its Use in Monitoring Free Fatty Acids," *The Journal of Biological Chemistry*, vol. 267, No. 33, pp. 23495-23501, Nov. 25, 1992.

Ruben, et al. "Serum Levels of Unbound Free Fatty Acids II: The Effect of Intralipid Administration in Premature Infants," *Journal of the American College of Nutrition*, vol. 16, No. 1, pp. 85-87, 1997.

Samanta, et al. "Possible Physiological Role of Myocardial Fatty Acid Binding Protein in Phospholipid Biosynthesis," *Journal of Lipid Mediators*, vol. 1, pp. 243-255, 1989.

Samanta, et a. "Free Radical Scavenging by Myocardial Fatty Acid Binding Protein," *Free Radical Research Communications*, vol. 7, No. 2, pp. 73-82, 1989.

She, et al. "The Substrate Specificities of Four Different Lysophospholipases as Determined by a Novel Fluorescence Assay," *Biochem J.*, vol. 298, pp. 23-29, 1994.

Victor, et al. "Myocardial Tissue Free Fatty Acids," *Journal of Molecular and Cellular Cardiology*, vol. 16, No. 8, pp. 709-721, Aug. 1984.

*Textbook of Cardiovascular Medicine*, Eric J. Topol, Editor; Lippincott-Raven Publishers, Philadelphia, PA, 1998. Chapter 16, Harvey D. White, "Unstable Angina-Ischemic Syndromes." pp. 365-393.

Brown, et al., "Fatty Acids and the Inhibition of Mitogen-Induced Lymphocyte Transformation by Leukemic Serum," The Journal of Immunology. vol. 131, No. 2, pp. 1011-1016, Aug. 1983.

Butko, et al. "Acidic Phospholipids Strikingly Potentiate Sterol Carrier Protein 2 Mediated Intermembrane Sterol Transfer," *Biochemistry.* vol. 29, pp. 4070-4077, 1990.

Bansal, et al. "Stroke During Pregnancy and Puerperium in Young Females Below the Age of 40 Years as a Result of Cerebral Venous/Venous Sinus Thrombosis," *Japanese Heart Journal*, vol. 21, No. 2, pp. 171-183, Mar. 1980.

Ageeva, et al. "Structural and Functional Characteristics of Red Cell Membranes in Patients with Ischemic Stroke and Dyscirculatory Encephalopathy," *Zhurnal Nevrologii I Psikhiatrii Imeni SS Korsakova*, vol. 94, No. 1, pp. 6-8, 1994. English Abstract.

Imre, et al. "Increased Proportion of Docosahexanoic Acid and High Lipid Peroxidation Capacity in Erythrocytes of Stroke Patients," *Stroke*, vol. 25, No. 12, pp. 2416-2420, 1994.

N. Bázan, et al. "Membrane Lipids in the Pathogenesis of Brain Edema: Phospholipids and Arachidonic Acid, the Earliest Membrane Components Changed at the Onset of Ischemia," *Advances in Neurology*, vol. 28: Brain Edema, Raven Press, New York, 1980, pp. 197-205.

N. Bázan, et al. "Effects of Ischemia and Electroconvulsive Shock on Free Fatty Acid Pool in the Brain," *Biochimica et Biophysica Acta*, 218, 1970, pp. 1-10.

M. Ikeda, et al. "Polyphosphoinositides as a Probably Source of Brain Free Fatty Acids Accumulated at the Onset of Ischemia," *Journal of Neurochemistry*, Raven Press, New York, 1986, pp. 123-132.

V. Kurien, "Serum-Free-Fatty-Acids After Acute Myocardial Infarction and Cerebral Vascular Occlusion," *The Lancet*, Jul. 16, 1966, pp. 122-127.

G. Richieri, et al., "Interactions of Long-Chain Fatty Acids and Albumin: Determination of Free Fatty Acid Levels Using the Fluorescent Probe ADIFAB," *Biochemistry*, vol. 32, 1993, pp. 7574-7580.

G. Richieri, et al. "Kinetics of Fatty Acid Interactions with Fatty Acid Binding Proteins from Adipocyte, Heart, and Intestine," *The Journal of Biological Chemistry*, vol. 271, No. 19, May 10, 1996, pp. 11291-11300.

B. Weinberger, et al. "Effects of Perinatal Hypoxia on Serum Unbound Free Fatty Acids and Lung Inflammatory Mediators," *Biology of the Neonate*, vol. 79, 2001, pp. 61-66.

Pelser, et al. "Fatty Acid-Binding Proteins as Plasma Markers of Tissue Injury," *Clinica Chimica Acta*, vol. 352, pp. 15-35, 2005.

Li, et al. "High Throughput Screening Systems for Identification of Fatty Acid Uptake Inhibitors," *FASEB Journal*, vol. 20, No. 4, Part 1, Mar. 2006.

Richieri, et al. "Fatty Acid Binding Proteins from Different Tissues Show Distinct Patterns of Fatty Acid Interactions," *Biochemistry*, vol. 39, No. 24, 7197-7204, 2000.

Richieri, et al. "The Measurement of Free fatty Acid Concentration with the Fluorescent Probe ADIFAB: A Practical Guide for the Use of the ADIFAB Probe," *Molecular and Cellular Biochemistry*, vol. 192, pp. 87-94, 1999.

Kampf, et al. "Fatty Acid Transport in Adipocytes Monitored by Imaging Intracellular Free Fatty Acid Levels," *The Journal of Biological Chemistry*, vol. 279, No. 34, pp. 35775-35780, Aug. 20, 2004.

Ikeda, et al. "Polyphosphoinositides as a Probable Source of Brain Free Fatty Acids, Accumulated at the Onset of Ischemia," *Journal of Neurochemistry*, vol. 47, No. 1, pp. 123-132, 1986.

Banaszak, et al. "Lipid-Binding Proteins: A Family of Fatty Acid and Retinoid Transport Proteins," *Advances in Protein Chemistry*, vol. 45, pp. 90-151, 1994.

van Zoelen, et al. "An Exact General Analysis of Ligand Binding Displacement and Saturation Curves," *Biochemistry*, vol. 32, pp. 6275-6280, 1993.

Veerkamp, et al. "Structural and Functional Features of Different Types of Cytoplasmic Fatty Acid-Binding Proteins," *Biochimica et Biophysica Acta*, vol. 1081, pp. 1-24, 1991.

Kohashi, et al. "Fluorescence Reaction of Bilirubin with Zinc Ion in Dimethyl Sulfoxide and Its Application to Assay of Total Bilirubin in Serum," *Analytica Chimica Acta*, vol. 365, Nos. 1-3, pp. 177-182, Jun. 5, 1998.

Sacchettini, et al. "The Structure of Crystalline Escherichia coli-Derived Rat Intestinal Fatty Acid-Binding Protein at 2.5-Å Resolution," *The Journal of Biological Chemistry*, Vo. 263, No. 12, pp. 5815-5819, Apr. 25, 1988.

Evans, et al. "The Chemical Modification of Cysteine-69 of Rat Liver Fatty Acid-Binding Protein (FABP): A Fluorescence Approach to FABP Structure and Function," *Molecular and Cellular Biochemistry*, vol. 98, Nos. 1-2, pp. 135-140, Oct. 1990.

Lowe, et al. "Expression of Rat Intestinal Fatty Acid-Binding Protein in *Escherichia coli*," *The Journal of Biological Chemistry*, vol. 262, No. 12, pp. 5931-5937, Apr. 25, 1987.

(56) References Cited

OTHER PUBLICATIONS

Huber, et al. "Fatty Acid-Specific Fluorescent Probes and Their Use in Resolving Mixtures of Unbound Free Fatty Acids in Equilibrium with Albumin" Biochemistry 45:14263-14274, 2006.

Bhardwaj, et al. "A Multicenter Comparison of Established and Emerging Cardiac Biomarkers for the Diagnostic Evaluation of Chest Pain in the Emergency Department," *American Heart Journal*, vol. 162, No. 2, pp. 276-282.e1, Aug. 2011.

* cited by examiner

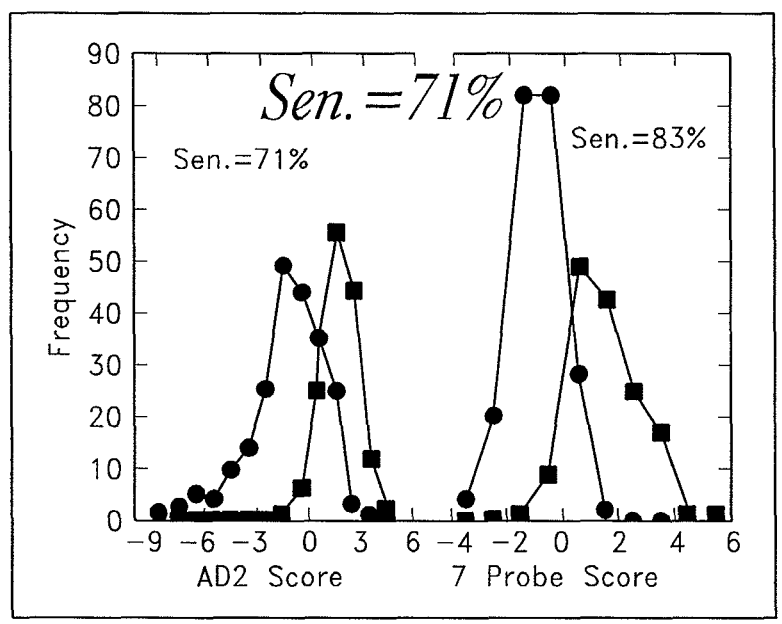
FIG. 1
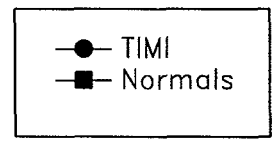

ROC curves show that multiple probes improve performance.

---- ADIFAB2 (AUC = 0.76)
—— 7 probes (AUC = 0.95)

Discriminant score is indicative of type of ACS.

■ EARLY samples

Disease-specific changes in the probe response profile.

1 L1P8H2
2 L2P22G6
3 L11P7B3
4 L13P7B43
5 ADIFAB2
6 L10P7A4
7 L18P5G12

SEQUENCE LISTING

<160> NUMBER OF SEQ ID NOS: 4

<210> SEQ ID NO 1
<211> LENGTH: 399
<212> TYPE: DNA
<213> ORGANISM: Rattus norvegicus
<220> FEATURE:
<221> NAME/KEY: CDS
<222> LOCATION: (1)...(399)
<223> OTHER INFORMATION: wild-type rat intestinal fatty acid binding protein cDNA sequence

<400> SEQUENCE: 1 atg gca ttt gat ggc act tgg aaa gta tac cgg aat gag aac tat gaa    48

```
Met Ala Phe Asp Gly Thr Trp Lys Val Tyr Arg Asn Glu Asn Tyr Glu
 1               5                  10                 15 aag ttc atg gag aaa atg ggc att aac gtg gtg aag agg aag ctt gga        96
Lys Phe Met Glu Lys Met Gly Ile Asn Val Val Lys Arg Lys Leu Gly
             20                  25                  30 gct cat gac aac ttg aaa ctg acg atc aca cag gaa gga aat aaa ttc       144
Ala His Asp Asn Leu Lys Leu Thr Ile Thr Gln Glu Gly Asn Lys Phe
         35                  40                  45 aca gtc aaa gaa tca agc aac ttc cga aac att gat gtt gtg ttt gaa       192
Thr Val Lys Glu Ser Ser Asn Phe Arg Asn Ile Asp Val Val Phe Glu
     50                  55                  60 ctc ggc gtc gac ttt gcc tat agt cta gca gat gga aca gaa ctc act       240
Leu Gly Val Asp Phe Ala Tyr Ser Leu Ala Asp Gly Thr Glu Leu Thr
 65                  70                  75                  80 ggg acc ttg acc atg gag gga aat aaa ctt gtt gga aaa ttc aaa cgt       288
Gly Thr Leu Thr Met Glu Gly Asn Lys Leu Val Gly Lys Phe Lys Arg
                 85                  90                  95 gta gac aat gga aag gag ctg att gct gtc cga gag att tct ggt aac       336
Val Asp Asn Gly Lys Glu Leu Ile Ala Val Arg Glu Ile Ser Gly Asn
             100                 105                 110 gaa cta atc caa acc tac aca tat gaa gga gtg gag gcc aag cgc atc       384
Glu Leu Ile Gln Thr Tyr Thr Tyr Glu Gly Val Glu Ala Lys Arg Ile
         115                 120                 125 ttt aag aag gaa tag                                                   399
Phe Lys Lys Glu *
     130

<210> SEQ ID NO 2
<211> LENGTH: 131
<212> TYPE: PRT
<213> ORGANISM: Rattus norvegicus
<220> FEATURE:
<221> NAME/KEY: PEPTIDE
<222> LOCATION: (1)...(131)
<223> OTHER INFORMATION: wild-type rat intestinal fatty acid binding
      protein
<220> FEATURE:
<221> NAME/KEY: ACETYLATION
<222> LOCATION: (1)...(1)

<400> SEQUENCE: 2

Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
             20                  25                  30

His Asp Asn Leu Lys Leu Thr Ile Thr Gln Glu Gly Asn Lys Phe Thr
         35                  40                  45

Val Lys Glu Ser Ser Asn Phe Arg Asn Ile Asp Val Val Phe Glu Leu
     50                  55                  60

Gly Val Asp Phe Ala Tyr Ser Leu Ala Asp Gly Thr Glu Leu Thr Gly
 65                  70                  75                  80

Thr Trp Thr Met Glu Gly Asn Lys Leu Val Gly Lys Phe Lys Arg Val
                 85                  90                  95

Asp Asn Gly Lys Glu Leu Ile Ala Val Arg Glu Ile Ser Gly Asn Glu
             100                 105                 110

Leu Ile Gln Thr Tyr Thr Tyr Glu Gly Val Glu Ala Lys Arg Ile Phe
         115                 120                 125

Lys Lys Glu
     130
```

```
<210> SEQ ID NO 3
<211> LENGTH: 426
<212> TYPE: DNA
<213> ORGANISM: Rattus norvegicus
<220> FEATURE:
<221> NAME/KEY: mutation
<222> LOCATION: (1)...(426)
<223> OTHER INFORMATION: rat intestinal fatty acid binding protein DNA
      sequence coding for substitution of alanine for
      leucine at position 72
<223> OTHER INFORMATION: 3' terminus codes for a 6his tag

<400> SEQUENCE: 3
atggcatttg atggcacttg gaaagtagac cggaatgaga actatgaaaa gttcatggag        60
aaaatgggca ttaacgtggt gaagaggaag cttggagctc atgacaactt gaaactgacg       120
atcacacagg aaggaaataa attcacagtc aaagaatcaa gcaacttccg aaacattgat       180
gttgtgtttg aactcggcgt cgactttgcc tatagtgctg cagatggaac agaactcacc       240
ggtacctgga caatggaggg aaataaactt gttggaaagt ttaaacgtgt agacaatgga       300
aaggagctga ttgctgtccg agagatttct ggtaacgaac taatccagac ctacacatat       360
gaaggagtgg aggccaagcg gatctttaag aaggaccgcg gtcatcatca ccatcatcac       420
tagtaa                                                                  426

<210> SEQ ID NO 4
<211> LENGTH: 139
<212> TYPE: PRT
<213> ORGANISM: Rattus norvegicus
<220> FEATURE:
<221> NAME/KEY: MUTAGEN
<222> LOCATION: (72)...(72)
<223> OTHER INFORMATION: rat intestinal fatty acid binding protein with
      alanine substitution for leucine at position 72 and Glu 131 to Asp
      subsitition.
<223> OTHER INFORMATION: COOH-terminal affinity tag comprising Arg132,
      Gly133 and 6 histidines

<400> SEQUENCE: 4

Ala Phe Asp Gly Thr Trp Lys Val Asp Arg Asn Glu Asn Tyr Glu Lys
1               5                   10                  15

Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60

Gly Val Asp Phe Ala Tyr Ser Ala Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Asp Arg Gly His His His His His
    130                 135
```

US 9,164,109 B2

USE OF PROBES FOR UNBOUND METABOLITES

RELATED APPLICATIONS

This application is the U.S. National Phase of PCT/UP2007/082725, filed Oct. 26, 2007 which claims priority to U.S. Application No. 60/958,344 filed Jul. 5, 2007, U.S. Application No. 60/899,231 filed Feb. 2, 2007, and U.S. Application No. 60/854,879, filed Oct. 27, 2006. All of the above-referenced applications are incorporated herein by reference.

STATEMENT REGARDING FEDERALLY SPONSORED R&D

This work was supported in part by Roadmap Grant No. R33DK070314 and SBIR Grant No. R43DK073535 from the National Institute of Health. Consequently, the U.S. government may have certain rights to this invention.

REFERENCE TO SEQUENCE LISTING

A sequence listing is included at the end of the specification.

BACKGROUND OF THE INVENTION

1. Field of the Invention

The invention relates to diagnostic methods to determine disease state, nutritional state, or effect of therapy by measurement of one or more unbound metabolites by measuring a fluorescence change upon binding to one or more probes. Preferably, the probes are fluorescently labeled muteins of intracellular lipid binding proteins (iLBP).

2. Description of the Related Art

Metabolomics is advancing rapidly as a result of new technologies and the expanding interest in systems biology (Goodacre, R. (2005) Metabolomics—the way forward, *Metabolomics* 1, 1-2) This advance is being driven by the recognition that physiologic phenotype is essentially a reflection of the metabolic profile, and therefore, metabolic profiling should provide an accurate representation of the states of health and disease. The activity of a given metabolite is frequently dictated by its solubility as a "free" or unbound molecule in aqueous bodily fluids. For many metabolites the unbound concentration represents a small fraction of the total, with most of the total metabolite bound in carrier complexes. Total metabolite concentrations are typically measured, but it is the unbound metabolite that interacts with targets such as protein receptors and cell membranes (for example, Sorrentino, D., et al. (1989) At physiologic albumin/oleate concentrations oleate uptake by isolated hepatocytes, cardiac myocytes, and adipocytes is a saturable function of the unbound oleate concentration, *J. Clin. Invest.* 84, 1325-1333). A profiling of unbound metabolite concentrations should therefore provide the most accurate measure of physiologic health.

For example, profiling unbound rather than total metabolites is especially relevant for the long chain free fatty acids (FFA), which play major roles in signaling, macromolecular structure and energy production. Long chain FFA are sparingly soluble, yet act through extra- and intra-cellular aqueous phases to bind to target macromolecules (Sorrentino, et al. supra; Cupp, D., et al. (2004) Fatty acid:albumin complexes and the determination of long chain free fatty acid transport across membranes, *Biochemistry* 43, 4473-4481; Kampf, J. P. et al. (2004) Fatty acid transport in adipocytes monitored by imaging intracellular FFA levels, *J. Biol. Chem.* 279, 35775-35780). In many instances, FFA-mediated signaling events can be abolished by adding fatty-acid-free bovine serum albumin, which reduces the unbound FFA ($FFA_u$) concentration without changing the total FFA concentration (Poitout, V. (2003) The ins and outs of fatty acids on the pancreatic beta cell, *Trends Endocrinol. Metab* 14, 201-203; Kleinfeld, A. M, et al. (2005) Free fatty acid release from human breast cancer tissue inhibits cytotoxic T lymphocyte-mediated killing, *J. Lipid Res.* 46, 1983-1990). Total serum concentrations of long chain FFA are in the millimolar range while FFA-protein receptor binding affinities are in the nanomolar range as are $FFA_u$ concentrations (Kampf, J. P., et al. supra; Richieri, G. V., et al. (1993) Interactions of long chain fatty acids and albumin: Determination of free fatty acid levels using the fluorescent probe ADIFAB, *Biochemistry* 32, 7574-7580; Richieri, G. V., et al. (1994) Equilibrium constants for the binding of fatty acids with fatty acid binding proteins from intestine, heart, adipose, and liver; measured with the fluorescence probe ADIFAB, *J. Biol. Chem.* 269, 23918-23930; Apple, F. S., et al. (2004) Unbound Free Fatty Acid Concentrations Are Increased in Cardiac Ischemia, *Clinical Proteomics* 1, 41-44). The hydrophobic nature of FFA and low $FFA_u$ concentrations have made it difficult to measure $FFA_u$ in biological fluids, and thus, total FFA is typically measured even though FFA-dependent signaling events are triggered by unbound rather than total FFA concentrations.

More than 40 different species of FFA with widely different biological activities have been identified in human serum (Yli-Jama, P., et al. (2002) Serum free fatty acid pattern and risk of myocardial infarction: a case-control study, *J Intern. Med.* 251, 19-28). Striking examples of their different biological activities include the induction of apoptosis in various cell types by palmitate (16:0) but not oleate (18:1) (de Vries, J. E., et al. (1997) Saturated but not mono-unsaturated fatty acids induce apoptotic cell death in neonatal rat ventricular myocytes, *J. Lipid Res.* 38, 1384-1394; Listenberger, L. L., et al. (2001) Palmitate-induced apoptosis can occur through a ceramide-independent pathway, *J. Biol. Chem.* 276, 14890-14895; Hickson-Bick, D. L., et al. (2002) Palmitate-induced apoptosis in neonatal cardiomyocytes is not dependent on the generation of ROS, *Am. J. Physiol Heart Circ. Physiol* 282, H656-H664) and the inhibition of cytotoxic T lymphocyte signaling by oleate (OA) but not palmitate (PA) (Kleinfeld, et al. supra; Richieri, G. V. et al. (1989) Free fatty acid perturbation of transmembrane signaling in cytotoxic T lymphocytes, *J. Immunol.* 143, 2302-2310). In addition, alterations in the profile of total plasma FFA have been reported in association with disease states (Yli-Jama, P., et al. supra; Lorentzen, B., et al. (1995) Fatty acid pattern of esterified and free fatty acids in sera of women with normal and pre-eclamptic pregnancy, *Brit. J. Obstetrics and Gynecology* 102, 530-537; Rodriguez de Turco, E. B., et al. (2002) Systemic fatty acid responses to transient focal cerebral ischemia: influence of neuroprotectant therapy with human albumin, *J Neurochem.* 83, 515-524; Yli-Jama, P., et al. (2002) Serum non-esterified very long-chain PUFA are associated with markers of endothelial dysfunction, *Atherosclerosis* 164, 275-281; Freedman, S. D., et al. (2004) Association of cystic fibrosis with abnormalities in fatty acid metabolism, *N. Engl. J. Med.* 350, 560-569).

Plasma $FFA_u$ levels are a reflection of the FFA-albumin binding equilibrium. The affinities of albumin for different FFA can differ by more than 2 orders of magnitude (Richieri, G. V., et al. (1993) supra; Spector, A. A. (1975) Fatty acid binding to plasma albumin, *J. Lipid Res.* 16, 165-179), and therefore, the equilibrium $FFA_u$ profile will differ from the total profile. $FFA_u$ profiles have not been reported previously because none of the available measurement techniques can resolve the nanomolar quantities of individual $FFA_u$ in the $FFA_u$ mixtures present in aqueous biological fluids. However, measurements of individual $FFA_u$ and/or average values for $FFA_u$ mixtures have been carried out previously using the acrylodan labeled fatty acid binding proteins ADIFAB and ADIFAB2 (Apple, et al. supra; Richieri, G. V. et al. (1995) Unbound free fatty acid levels in human serum, *J. Lipid Res.* 36, 229-240).

DEFINITIONS

For purposes of the present disclosure, "fatty acids" are non esterified carboxylated alkyl chains of 1-30 carbons atoms which may exist as neutral (e.g. protonated, sodium or potassium salt) or ionic species, depending upon the pH and conditions of the aqueous media. "Free fatty acids (FFA)" are equivalent to fatty acids and both terms refer to the totality of FFA including those in aqueous solution as monomers plus those that are not in solution (for example bound to other macromolecules (proteins, membranes), cells or part of an aggregate of FFA (micelles, soaps and other more complex aggregates). FFA present as monomers in aqueous solution (either charged or neutral) are referred to as "unbound free fatty acids (FFAu)".

For purposes of the present disclosure, "metabolites" are physiologically important molecules whose molecular weight is approximately 2000 Da or less. These include molecules that occur naturally in the course of human or animal physiology or pathophysiology, and drug molecules and their metabolic products and nutrient molecules and their metabolic products. Similar to FFA and depending upon their solubility, a fraction of each metabolite is present as monomers in aqueous solution (either charged or neutral). We refer to this fraction as the "unbound metabolite".

For the purposes of the present disclosure, "probes" are fluorescently labeled proteins that reveal a measurable change in fluorescence upon binding to an analyte such as an unbound metabolite, for example, an $FFA_u$.

U.S. Pat. No. 5,470,714 and U.S. Pat. No. 6,444,432, which are incorporated herein by reference, describe probes for the determination of unbound free fatty acids (FFAu). These probes were constructed using either native or mutant forms of proteins from the Intracellular lipid binding proteins (iLBPs) family that includes FABPs (Banaszak et al (1994) Adv. Protein Chem. 45:89-151; Bernlohr et al (1997) Ann. Rev. Nutrition, 17: 277-303). FABPs are intracellular proteins of approximately 15 kDa molecular weight and have a binding site that binds 1 or 2 FFA.

Fluorescently labeled fatty acid binding proteins (probes) that display specificity for the 5 FFA that are among the most abundant in human plasma (PA, OA, linoleate (LA), stearate (SA) and arachidonate (AA)) and their use to generate metabolic profiles are described. These probes have sufficient specificity and sensitivity to resolve individual $FFA_u$ in $FFA_u$ mixtures. The probes were constructed by labeling site-specific mutants of the rat intestinal fatty acid binding protein (rI-FABP, SEQ ID NO: 2) or the six histidine tagged L72A mutant of rI-FABP (SEQ ID NO: 4). A specific probe for detection of unbound unconjugated bilirubin (UCB) is also described. Profiles generated using these probes are useful in detection and monitoring of human diseases, including but not limited to, cardiac dysfunction, especially myocardial infarction and liver disorders, especially neonatal jaundice or hyperbilirubinemia.

SUMMARY OF THE INVENTION

Embodiments of the invention are directed to a methods of determining a sample response profile of one or more probes of unbound metabolites in body fluids for a test individual which includes one or more of the following steps:
  obtaining a body fluid sample from the test individual;
  measuring a sample response for each of the one or more probes to the body fluid sample to generate a sample response profile; and
  applying a statistical classification analysis to determine the probability that the sample response profile corresponds to a state different from a state of a preselected control population.

In some embodiments, the preselected control population includes individuals without disease symptoms and the test individual is a patient presenting with symptoms of the disease. In some alternate embodiments, the preselected control population includes individuals who have not been treated with a test drug and the test individual is an individual who has been treated with the test drug. In some alternate embodiments, the preselected control population includes individuals who have not been administered with test nutrients and the test individual is an individual who has been administered with test nutrients.

In preferred embodiments, the body fluid is whole blood, blood plasma, blood serum, urine, cerebrospinal fluid (CSF), saliva, gastric juices, bile, amniotic fluid, breast milk, seminal fluid, interstitial fluid, synovial fluid, plant sap or lymph.

In preferred embodiments, the statistical classification analysis is a mathematical method for classifying results into distinct groups, which is used to determine the probability that the response profile corresponds to the state of the preselected control population. Preferably, the statistical classification analysis method is principal component analysis, discriminant analysis, decision trees, logistic regression, support vector machines, k-nearest neighbors, classification analysis based on Bayesian decision theory, analysis based on artificial neural networks techniques or a mathematical method for pattern recognition or for classifying metabolomic results.

In preferred embodiments, the unbound metabolite is an unbound free fatty acid $(FFA)_u$ or free unconjugated bilirubin $(UCB)_f$.

In preferred embodiments, the one or more probes include at least two probes which are proteins labeled with a fluorophore that generate a fluorescence change upon binding unbound metabolites. In preferred embodiments, the proteins are intestinal lipid binding protein muteins. More preferably, the proteins are fatty acid binding protein muteins. Yet more preferably, the fatty acid binding protein muteins are selected from ADIFAB2 (L72A mutein relative to SEQ ID NO: 2) and fatty acid binding proteins that have mutations in at least two positions which include position 14, 18, 21, 31, 38, 72, 73, 78, 102, 106, 115, and 117 relative to the L72A mutein of the rat Intestinal-FABP shown as SEQ ID NO: 2. In a most preferred embodiment, the combination of probes includes at least two selected from L1P8H2, L2P22G6, L10P7A4, L11P7B3, L13P7B4, L18P5G12 and ADIFAB2. In preferred embodiments, the fluorophore is acrylodan.

In preferred embodiments, the unbound metabolites are associated with a carrier macromolecule, whereby the carrier macromolecule complexes with the unbound metabolite.

Preferably, the carrier macromolecule is albumin, lipid binding proteins, lipid vesicles or cyclodextrins. More preferably, the carrier macromolecule is human serum albumin (HSA) or bovine serum albumin (BSA).

In preferred embodiments, the method includes the step of comparing a fluorescence index, which may include changes in intensity, ratio of intensities at two excitation and/or emission wavelengths, polarization and/or lifetime of the probes for the body fluid sample compared to the preselected control population. Preferably, the fluorescence indices obtained are analyzed by cluster analysis and/or by discriminant analysis to obtain a diagnosis. In preferred embodiments, the method further includes analyzing the fluorescence indices obtained by pattern recognition to obtain a diagnosis.

Embodiments of the invention are directed to where the sample response for each of the one or more probes is calculated as $\Delta R/Ro$, or the logarithm of $\Delta R/Ro$ and where R is the fluorescence emission ratio ($I_{550}/I_{457}$) in plasma, $R_o$ is the fluorescence ratio of the probe with no fatty acids-present, and $\Delta R$ is the difference between R and Ro.

Embodiments of the invention are directed to where the sample response for each of the one or more probes is calculated as $\Delta R/(Rmax-R)$, or the logarithm of $\Delta R/(Rmax-R)$ and where R is the fluorescence emission ratio ($I_{550}/I_{457}$) in plasma, $\Delta R$ is the difference between R and Ro, $R_o$ is the fluorescence ratio of the probe with no fatty acids present, and Rmax is the fluorescence ratio ($I_{550}/I_{457}$) of the probe when the probe is saturated with FFA.

In preferred embodiments, the fluorescence indices are analyzed by pattern classification methods or by discriminant analysis to obtain a diagnosis.

In preferred embodiments, the body fluid sample is from a patient with symptoms of cardiac dysfunction, non-alcoholic fatty liver disease (NAFLD), stroke, sepsis, or diabetes and the preselected control population is one or more individuals without symptoms of cardiac dysfunction, non-alcoholic fatty liver disease (NAFLD), stroke, sepsis, or diabetes. Preferably, the cardiac dysfunction is acute coronary syndrome. In a preferred embodiment, the method includes one or more of the following steps:

withdrawing a fluid sample from the patient;
contacting the fluid sample with at least two probes which are L1P8H2, L2P22G6, L10P7A4, L11P7B3, L13P7B4, L18P5G12 or ADIFAB2;
measuring the change in fluorescence of the probes;
determining the binding of at least two FFAu in the fluid sample from the measured change in fluorescence;
comparing the probe binding in the sample to probe binding in a normal population, without symptoms of cardiac dysfunction, non-alcoholic fatty liver disease (NAFLD), stroke, sepsis, or diabetes using statistical classification analysis; and
correlating the probe binding with the presence or absence of cardiac dysfunction, non-alcoholic fatty liver disease (NAFLD), stroke, sepsis, or diabetes in the patient.

Preferred embodiments of the invention are directed to methods to determine the concentration of free unconjugated bilirubin (UCBf) in body fluids of a mammal which include one or more of the following steps:

withdrawing a body fluid from the mammal;
contacting the body fluid with a probe capable of binding to $UCB_f$; and
determining the level of $UCB_f$ by measuring binding to the probe and comparing to a standard.

In preferred embodiments, the body fluid is blood plasma. In preferred embodiments, the probe is a fatty acid binding protein mutein. Preferably, the FABP mutein is L24P19C7 which has the following mutations with reference to the L72A mutein of rat Intestinal Fatty Acid Binding Protein (SEQ ID NO: 4): Y14R M18L L38V V60R A72L A73F R106C Q115R and Y117D. In preferred embodiments, the mammal is a human.

Embodiments of the invention are directed to a substrate which includes a support and an array on the support with two or more probes. In preferred embodiment, the probes are L1P8H2, L2P22G6, L10P7A4, L11P7B3, L13P7B4, L18P5G12, L24P19C7 and/or ADIFAB2 attached to the support. Preferably, each probe is provided in duplicate pairs on the support. In preferred embodiments, the support is a slide, dish or multiwell plate. Most preferably, the support is a multiwell plate and the two or more probes are attached to different wells of the multiwell plate by Ni-His tag interaction. Embodiments of the invention are directed to a kit which includes the substrate with a support and array with two or more probes as described above and at least two FFAu standards.

Embodiments of the invention are directed to a method of diagnosing a coronary dysfunction, non-alcoholic fatty liver disease (NAFLD), stroke, sepsis, or diabetes including one or more of the following steps:

obtaining a blood sample from a mammal;
contacting the blood sample with one probe from the probes on the substrate described above;
determining a fluorescence index for each probe;
comparing the fluorescence index for each probe bound to the blood sample with the fluorescence index for each probe not bound to blood sample to obtain a change in fluorescence index;
analyzing the change in fluorescence index for each probe by cluster or classification analysis by comparison to a control population that does not have coronary dysfunction, non-alcoholic fatty liver disease (NAFLD), stroke, sepsis, or diabetes; and
diagnosing coronary dysfunction, non-alcoholic fatty liver disease (NAFLD), stroke, sepsis, or diabetes in the mammal.

In preferred embodiments, the diagnostic methods as described are applied to mammals, preferably humans.

Embodiments of the invention are directed to methods for diagnosis of different degrees of acute coronary syndromes (ACS) by comparing a sample response profile to classifying functions determined from multi-probe profiles of patients with different degrees of ACS. In preferred embodiments, the classification functions are determined from patients with unstable angina, non ST elevation myocardial infarction and/or ST elevation myocardial infarction.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 1 shows that measurements with multiple probes improves sensitivity relative to measurements with ADIFAB2 alone in the detection of cardiac dysfunction in TIMI II patients. The left panel shows the distribution of discriminant scores for measurements with ADIFAB2 only and the right hand panel with the 7 probes of Table 1.

FIG. 9 shows the average change (+ standard error) in probe response from healthy to each disease state. Multivariate analysis indicates that differences between all probe profiles are significant (p<0.05).

DETAILED DESCRIPTION OF THE PREFERRED EMBODIMENT

Figure 2:
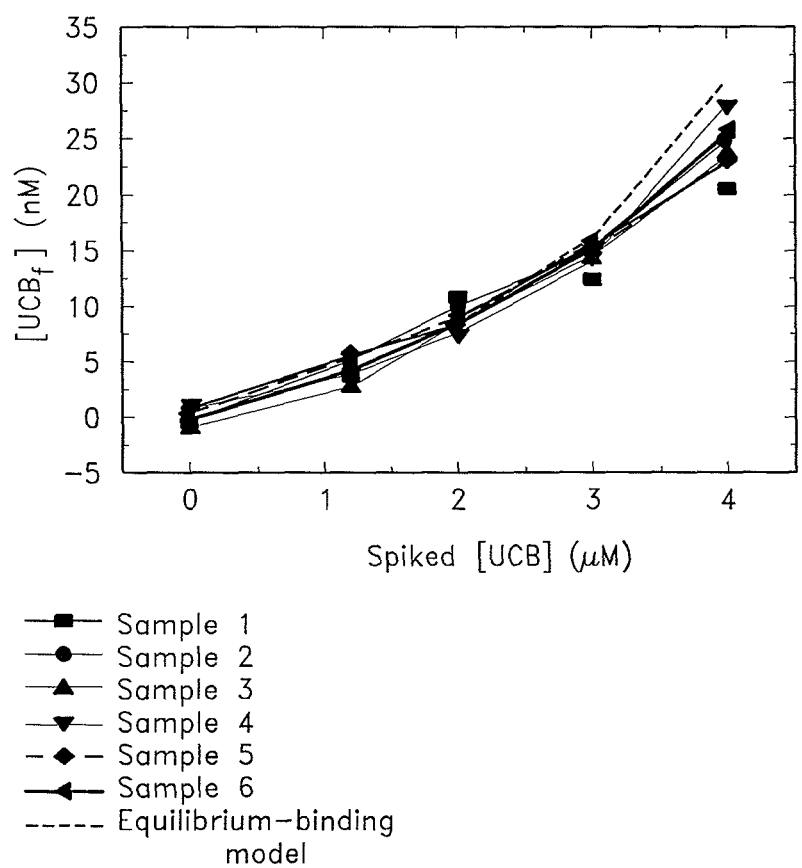
FIG. 2 shows L24P19C7 measurement of [UCB$_f$] in adult plasma spiked with UCB (average [HSA]~6.5 μM). The model values were calculated using a $K_d^{HSA}$=19 nM and [HSA]=6.5 μM.

Probes are proteins that have been 'labeled' through the covalent addition of a fluorescent molecule (fluorophore) to a specific site on the protein and that bind metabolites. Probes have the characteristic that their fluorescence changes in a measurable way when they bind metabolites. Different probes are generated by mutating the starting (template) protein and labeling the mutated proteins (muteins) with a fluorophore. The ability of each such probe to respond to a particular metabolite (or analyte) can then be assessed by measuring the change in fluorescence upon addition of defined concentrations of the unbound metabolite. The fluorescence responses to a set of defined metabolites constitutes the "probe response profile" or the "response profile of the probe" to that set of metabolites.

In a preferred embodiment, a protein that is capable of binding one or more unbound metabolites may be used as a template for mutagenesis. In some preferred embodiments, the protein capable of binding one or more unbound metabolites includes intracellular lipid binding proteins (iLBP), serum albumins, acyl CoA binding proteins, phospholipid or glycolipid binding proteins, retinol/retinoic acid binding proteins, bile salt binding proteins, an antibody or a Fatty Acid Binding Protein (FABP). The protein may bind fatty acids, other metabolites or both fatty acids and other metabolites. Besides unbound free fatty acids (FFA)$_u$ and free (unbound) unconjugated bilirubin (UCB)$_f$, possible metabolites include but are not limited to molecules such as metabolites of FFA, drugs, drug metabolites, hormones, prostaglandins, leukotrienes, sphingosine, sphingolipids, phospholipids, glycolipids, metabolites of sphingolipids, phospholipids, glycolipids, di and monoglycerols, cholesterol and cholesterol derivatives and other steroids, lipid-soluble vitamins, bile salts such as bilirubin, enzyme cofactors, retinoids such as retinoic acid and retinal, heme and heme metabolites, amino acids, peptides, carbohydrates and multivalent ions.

In more preferred embodiments, an FABP gene, wild-type or mutant, is used as the initial template or starting point for mutagenesis. A collection of mutant FABP clones is generated from the template. In preferred embodiments, mutation involves one or more amino acid substitutions in the binding cavity or the helical cap of the FABP. In a preferred embodiment, a mutant Rat Intestinal Fatty Acid Binding Protein (rI-FABP), which has approximately 130 amino acid residues, was used as the starting point for the mutagenesis.

DNA and protein sequences for Fatty Acid Binding Proteins (FABPs) are shown in the sequence listing. SEQ ID NO: 1 shows the cDNA and amino acid sequences for the wild-type rat intestinal Fatty Acid Binding Protein (rIFABP). The rat fatty acid binding protein is post-translationally modified in the rat, with the modifications including the removal of the N-terminal methionine and the acetylation of the "new" N-terminal residue Ala. Protein sequences are numbered starting with the first residue of the mature protein. Thus, Ala is residue 1 in the corresponding protein shown as SEQ ID NO: 2. In a preferred embodiment, the protein has a substitution of the native leucine with alanine at position 72 and the resulting probe is termed ADIFAB2.

SEQ ID NO: 3 shows a preferred template rI-FABP-L72A, E131D with a COOH-terminal affinity tag comprising Arg132, Gly133 and 6 histidines according to the invention. SEQ ID NO: 4 shows the corresponding protein sequence.

Any number of mutagenesis methods may be used to generate a collection or "library" of mutants, said mutagenesis methods include but are not limited to error-prone PCR, site-directed mutagenesis using defined or degenerate oligonucleotides, splicing by overlap extension (SOE), gene shuffling, or the use of mutator host strains. A preferred method is oligo-directed PCR-based mutagenesis using SOE.

Mutant genes are introduced into an organism capable of producing soluble protein from the mutant gene. Any type of organism can be used as long as soluble protein can be harvested from the lysed cells or the cell growth medium. The protein may be expressed in bacteria, yeast, insect or other eukaryotic cells.

Protein purification is accomplished by incubating lysate from each clone with a solid support to which the protein is specifically bound with high affinity. The protein may associate with a solid support by immobilizing antibodies on the solid support, said antibodies having a high binding-affinity for the protein of interest.

Alternatively the protein may be "tagged" so that it binds to the support material with high affinity. This includes but is not limited to tagging with biotin, Flag-epitope or c-myc epitope or HA-tag, glutathione-S-transferase (GST), maltose binding protein (MBP), a chitin binding domain (CBD), Thioredoxin, β-Galactosidase, VSV-Glycoprotein, calmodulin binding protein, or a metal affinity tag such as a 6×His tag. Preferably, the fusion partner does not change the FABP metabolite binding properties. The specific association of the affinity tag with the solid support material enables single step purification of the protein of interest from the lysate. The affinity tag(s) may be fused at either the NH2- or COOH— termini or at both termini simultaneously. In a preferred embodiment, a 6× Histidine tag was fused to either the FABP NH$_2$— or COOH— termini or at both termini simultaneously without significantly changing the protein's fatty acid binding properties.

These fusion proteins can be reversibly immobilized on a solid support for protein purification, delipidation and probe production.

In a preferred embodiment, the template FABP is recombinant rat intestinal fatty acid binding protein (rI-FABP). Derivatization with acrylodan is performed using known methods substantially as previously described (U.S. Pat. No. 5,470,714 which is incorporated by reference & Richieri, G. V, et al., J. Biol. Chem., (1992) 276: 23495-23501). The wavelength emitted by the fluorescently-labeled FABP depends upon the fluorophore and protein used.

In one embodiment, the protein is purified and delipidated by passing through various types of 'standard' purification matrices (i.e. size exclusion chromatography, ion exchange chromatography, hydrophobic interaction chromatography (HIC)). The resulting purified and delipidated protein then undergoes a buffer exchange process to place it in the fluorophore reaction buffer. After the labeling reaction, the labeled protein is subjected to several HIC chromatography steps to remove unreacted fluorophore.

In an alternate embodiment, the muteins are affinity purified and left on the affinity purification matrix, essentially making the protein part of the solid phase. Chemical functionalities required for delipidation, labeling, and removal of unreacted label are passed over the protein/solid phase.

In preferred embodiments, the protein variants are labeled with acrylodan while still bound to the solid support. However other fluorescent labels may also be used such as but not limited to danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA). Other protein probes that bind unbound metabolites such as unbound FFA and that change their fluorescence upon binding may also be used including, but not limited to, albumin. Albumin with a fluorescent label such as 7-hydroxycoumarin or anthraniloyl changes its fluorescence upon binding FFA (Demant, E, Anal. Biochem. (1999) 267:366-372, Massey, J. B., et al Biophys. J. (1996) 72:1732-1743). Any fluorescent label may be used in the practice of the invention as long as a measurable difference may be detected upon binding of a free fatty acid or other analytes.

ADIFAB2 is rI-FABP that has Ala substituted for Leu at position 72 (rI-FABP-L72A). The wavelength at the maximum intensities emitted by fluorescently-labeled I-FABP's in the absence of FFA is about 420 to 480 nm. The emission wavelengths at the maximum intensities emitted by fluorescently-labeled I-FABP's with FFA bound is about 495 to 580 nm. Experiments typically involve measuring the fluorescence response within both emission maxima or at wavelengths for which the effect of interfering molecules such as hemoglobin can be eliminated as described in U.S. Pat. No. 6,999,173 which is incorporated herein by reference, and calculating the ratio 'R' of the two fluorescence intensities. The baseline value for this ratio, measured in the absence of analyte, is designated Ro.

The probes described according to some embodiments of the invention have altered specificity for different FFAu or other unbound metabolites relative to ADIFAB2. Altered specificity refers to an alteration in the fluorescence change that occurs when the probe is exposed to different unbound metabolites or different molecular species of FFAu (for example different chain lengths and/or different numbers of double bond and/or different rotational isomers about a given double bond and/or different locations of double bonds.) For example, ADIFAB2 might reveal, when exposed to a particular FFAu1 at a concentration of [FFAu1], a change ($\Delta R1$) in the value of the ratio R relative to Ro. Exposing ADIFAB2 to n different such FFAu would reveal a set of responses, $\{\Delta Ri\}=\Delta R1i, \Delta R2i, \ldots \Delta Rni$. This set of responses $\{\Delta Ri\}$ is defined as the "response profile for probe i" also termed "probe i response profile". A different probe with altered specificities would possess a different set of responses to the same set of n FFAu and concentrations; $\{\Delta Rj\}=\Delta R1j, \Delta R2j, \ldots \Delta Rnj$. Therefore $\{\Delta Rj\}$ is the response profile for probe j. With sufficient numbers of different probes possessing different responses it is possible by measuring the response of each probe to a sample containing mixtures of different FFAu and/or different unbound metabolites, to determine the concentration of each different FFAu and/or other unbound metabolites (see for example Example 1 and Huber, H. A., et al (2006) Fatty acid-specific fluorescent probes and their use in resolving mixtures of different unbound free fatty acids in equilibrium with albumin Biochemistry 45, 14263-14274). The set of responses for N different probes obtained in a single sample s containing an unknown mixture of different metabolites is $\{\Delta R^k\}s=\Delta R^1, \Delta R^2, \ldots \Delta R^N$ and $\{\Delta R^k\}s$ is defined as the "sample s response profile" or the "response profile of sample s". $\Delta R^1, \Delta R^2$ refer to the response profiles of probes 1 and 2, respectively. Because different states of health and disease might alter the distribution of different FFAu and/or different unbound metabolites in a variety of body fluids including but not limited to whole blood, blood plasma, blood serum, urine, cerebrospinal fluid (CSF), saliva, gastric juices, interstitial fluid, synoidal fluid or lymph, such a determination provides valuable information about health status. In addition, such measurements would provide valuable tools for basic research and drug discovery.

A collection of N probes with distinct signaling properties can be used to determine in a sample the set of responses each normalized to the Ro value of the probe. this is a first sample s1 response profile normalized to Ro: $\{\Delta R^k/Ro^k\}s1=(\Delta R^1/Ro^1, \Delta R^2/Ro^2, \ldots \Delta R^N/Ro^N)s1$ for the N probes in a mixture of unbound metabolites. The number of probes, N may be any number, in a preferred embodiment is 1, 2, 3, 4, 5, 6, 7, 8, 9, or 10 probes although more than 10 probes may be used. In some preferred embodiments, at least 2 probes are used. This response profile will be characteristic of the mixture of unbound metabolites in a particular sample s1 so that a different sample s2 with a different mixture would yield a different response profile. That is, $\{\Delta R^k/Ro^k\}s2=(\Delta R^1/Ro^1, \Delta R^2/Ro^2, \ldots \Delta R^N/Ro^N)s2$.

A collection of probes with distinct signaling properties can be used to determine the concentrations of different unbound metabolites in a mixture, for example the concentrations of different unbound free fatty acids in a mixture. Thus, an unbound metabolite and/or an unbound free fatty acid profile can be determined for an individual. The most complete profile for fatty acids is the enumeration of the concentrations of each of the unbound free fatty acids in a mixture. This type of profile will require at least N different probes for n fatty acids, where N is greater than or equal to n. Less detailed, but very informative profiles, such as the enumeration of the fractions of different fatty acid classes, can be determined with fewer distinct probes (N probes for n classes). Classes of unbound free fatty acids include saturated, unsaturated, monounsaturated, polyunsaturated, short chain, medium chain, long chain and very long chain. In a preferred embodiment, the concentration of each type of unbound FFA in a mixture is determined. In another preferred embodiment, the fraction of unbound FFA that are unsaturated is determined. In another preferred embodiment, the fraction of FFAu that are monounsaturated is determined. In another preferred embodiment, the fraction of FFAu that are polyunsaturated is determined. In another preferred embodiment, the fraction of FFAu that are saturated is determined. In another preferred embodiment, the fraction of FFAu that are short chain (4-8 Carbon length) is determined. In another preferred embodiment, the fraction of FFAu that are medium chain (10-14 Carbon length) is determined. In another preferred embodiment, the fraction of FFAu that are long chain (16+ Carbon length) is determined. In another preferred embodiment, the fraction of FFAu that are very long chain (20+ Carbon length) is determined. In a preferred embodiment, levels of palmitate, oleate, stearate, linoleate and arachidonate are determined to obtain an unbound metabolic profile for an individual. Such determinations are used to generate, for any individual, a profile of unbound FFA that may be useful in the diagnosis of disease and the determination of risk factors for disease. Such diseases include but are not limited to cardiac disease or dysfunction, stroke, NAFLD, sepsis, neurological diseases such as dementia and Alzheimer's disease, diabetes, inflammatory diseases and certain cancers.

In preferred embodiments of the invention, the sample used for the determination of unbound FFA is a fluid sample derived from a human, an animal or a plant. Preferably, the fluid is whole blood, blood plasma, blood serum, urine, CSF, saliva, gastric juices, interstitial fluid, lymph or plant sap. In some embodiments, unbound metabolites such as unbound FFA are extracted from tissue samples by means known in the art. In other embodiments the determination of unbound metabolites such as unbound FFA is performed within the cytoplasm of a cell by microinjecting or otherwise transfecting the probes into cells. Unbound metabolites include but are not limited to unbound FFA, metabolites of FFA, drugs, drug metabolites, hormones, prostaglandins, leukotrienes, sphingosine, sphingolipids, phospholipids, glycolipids, metabolites of sphingosine, sphingolipids, phospholipids, glycolipids, and di and monogylcerides, cholesterol and cholesterol derivatives and other steroids, lipid-soluble vitamins, bile salts, enzyme cofactors, retinoids such as retinoic acid and retinal, heme and heme metabolites, amino acids, peptides, carbohydrates and multivalent ions. As discussed above, classes of unbound free fatty acids include saturated, unsaturated, monounsaturated, polyunsaturated, short chain, medium chain and long chain FFA.

A normal range for a given unbound metabolite is determined from a healthy population and deviations from this normal range may indicate disease. For example, elevated levels of unbound FFA are indicative of cardiac disease. Embodiments are directed to determination of a unbound metabolic profile for an individual using more than one probe to determine levels of more than one unbound metabolite. Unbound metabolic profiles from a normal, healthy population are determined. Deviations from a normal unbound metabolic profile are indicative of disease, nutrient deficiency, exposure to toxins or carcinogens and the like.

In one embodiment the sample response profile $\{\Delta R^k/R o^k\}$s is determined in a fluid sample from a population of individuals that does not have an ischemic condition to define the distribution of normal sample response profiles. The sample response profiles are generated using probes shown in Table 1 below. In one embodiment if the sample response profiled in a body fluid taken from a patient is significantly different than from the normal sample response profile obtained from the normal population, then an ischemic condition is indicated. Depending upon the number of different probes used and the characteristics of each of the probes, the sample response profile in a sample of body fluid may be converted into a collection of concentrations of unbound metabolites. In one embodiment, the sample response profile is the collection of concentrations for a set of FFAu. Statistical methods are then applied to compare profiles of the test group to profiles obtained from control patients.

In one embodiment, any assay that provides an indication of the level of at least two unbound free fatty acids ($FFA_u$) in body fluid relative to an asymptomatic population may be used to detect an ischemic condition. Normal values for each FFAu are determined from a population that does not have an ischemic condition. In one embodiment, if the levels of two or more $FFA_u$ in a body fluid are significantly different than the concentration of those two or more $FFA_u$ in the body fluid of a control population that does not have an ischemic condition, then an ischemic condition is indicated.

In some embodiments, probes produced as described above are used to determine the effect of a drug on a known unbound metabolic profile, more generally, the sample response profile. The unbound metabolic profile is determined for a test population which may be a normal or non-normal population such as a diseased population. For example, a metabolic profile may be determined for a diseased test population. The diseased test population could then be treated with a drug for a predetermined period of time. The unbound metabolic profile is then redetermined for the test population after drug treatment to observe the effect of the drug on the unbound metabolic profile. In some cases, a change in the unbound metabolic profile may be undesirable, for example, if testing a drug for toxicity and/or unwanted side effects. In other embodiments, a change in metabolic profile may indicate the effectiveness of the drug tested.

In some embodiments, a drug therapy in a diseased patient is monitored using one or more probes prepared according to the invention. For example, a body fluid may be withdrawn from the patient. Binding of an unbound metabolite indicative of a disease may be tested using at least one probe as described herein to generate a response profile. An abnormal level of one or more unbound metabolites is an indicator of a disease state. For example, elevated free fatty acids are risk factors and indicators of cardiovascular disease; deficiencies in vitamins B6 and folic acid have also been associated with cardiovascular disease and cancer. Levels of the unbound metabolites may be measured or monitored according to the invention.

In addition to diagnosing the presence of disease, levels of unbound metabolites may predict risk of future deleterious events. Moreover, these unbound metabolites, at sufficient levels, may themselves mediate cellular effects that result in deleterious outcomes. For example, a large long term study of apparently healthy men revealed that increasing levels of total serum free fatty acids (FFA), although within the normal range, were associated with an increased risk of sudden death 22 years later. It was speculated that this increased rate of death was a consequence of FFA induced cardiac arrhythmias. In another example, use of the combination of glucose-insulin-potassium (GIK) in patients suffering from acute myocardial infarcts, produced a significant reduction in mortality relative to patients who did not receive GIK. One theory for this beneficial effect is the reduction in serum total FFA produced by GIK. Thus there is a need to be able to monitor unbound metabolites to evaluate longer term risk of disease.

In some embodiments, the sample response profile or the unbound metabolic profile may be used to determine the effect of specific nutrients on an individual. An unbound metabolic profile may be used to indicate a nutrient deficiency.

In some embodiments, a unbound metabolic profile may be used to classify individuals into different categories having different susceptibilities to different drugs and/or nutrients. In preferred embodiments, principal component or other statistical classification methods may be used to cluster unbound metabolite profiles into defined groups.

Probe for Free Unconjugated Bilirubin ($UCB_f$).

Neonatal jaundice caused by hyperbilirubinemia occurs in 60-70% of newborns. (Dennery P A, Rhine W D and Stevenson D K. Clin Pediatr (Phila) 34: 103-107, 1995). Hyperbilirubinemia significantly increases the risk of neurologic damage the most severe form of which (kernicterus) can lead to irreversible brain damage and death. Therefore those neonates at risk for severe hyperbilirubinemia need to be identified. Current diagnostic techniques commonly measure total serum levels of conjugated and unconjugated bilirubin (UCB), but only unconjugated hyperbilirubinemia is associated with kernicterus and other forms of neurologic dysfunction. Only free (not bound to serum albumin) otherwise designated "unbound" UCB determines risk of bilirubin neurotoxicity. The free UCB ($UCB_f$) provides a more accurate assessment of the risk of neurologic dysfunction than the total serum bilirubin in part because a variety of factors lead to sharp increases in $UCB_f$ without significant changes in UCB (Funato M, Tamai H, Shimada S and Nakamura H. Vigintiphobia, unbound bilirubin, and auditory brainstem responses. *Pediatrics* 93: 50-53, 1994) for much the same reasons that FFAu is more sensitive to changes in homeostasis than is total FFA. Therefore, a method to accurately and easily determine the $UCB_f$ concentration in the clinical setting is needed.

A simple and rapid assay for [$UCB_f$] determination is described. A UCB-specific probe was developed through a process of iterative mutations and high throughput screening of fluorescently labeled fatty acid binding proteins. This probe can detect physiologic concentrations (nanomolar) of $UCB_f$ in plasma and is insensitive to a number of potential interfering ligands, including free fatty acids. This assay can be used for the detection of $UCB_f$ in plasma for the diagnosis of neonatal hyperbilirubinemia, for the study of bilirubin neurotoxicity and for improving the implementation of phototherapy in neonates undergoing treatment for hyperbilirubinemia.

The methods and probes described herein may be used to a) diagnose disease, b) monitor treatment therapies, c) assess nutritional challenges, d) assist in drug development by monitoring metabolite changes in cells and test animals to discover unwanted effects at early stages in development and e) profile demographic groups to assess differences in their susceptibility to different diseases, therapies, nutritional changes and environmental perturbations. The described methods and probes measure the level of the unbound (aqueous soluble) fraction, which is where many, if not most, physiologic changes and effects occur.

Statistical Analysis

Any method of statistical analysis may be used which allows classification of data into distinct groups. Such methods include but are not limited to methods of regression analysis, principal component analysis, discriminant analysis, and classification analysis based on Bayesian decision theory. Software programs are available to carry out these analyses, for example SPSS or XLSTAT, an Microsoft Excel add in.

EXAMPLES

Example 1

Resolving $FFA_u$ Profiles in Mixtures of FFA and Albumin

As a first step towards the determination of blood plasma $FFA_u$ profiles, 6 specific probes which are muteins of SEQ ID NO: 4 were used to profile mixtures of 4 and 5 FFA in equilibrium with bovine serum albumin (BSA) (Table 1). Because there is no independent method to determine $FFA_u$ concentrations, we also calculated the expected profiles from the known amounts of FFA and BSA used to generate the mixtures. These calculations required binding constants for each BSA-FFA interaction and a new BSA-binding model. Our measurements indicate that, to a good approximation, the binding of each of the FFA to BSA can be described in terms of a single class of 6 to 7 independent sites. Using this simple model, we have calculated $FFA_u$ profiles for mixtures of 4 and 5 FFA in equilibrium with BSA and compared these predictions to $FFA_u$ profiles measured with our probes. Good agreement was found between these two independent profiling methods (Table 2).

TABLE 1

Mutations present in ADIFAB2 relative to rI-FABP (SEQ ID NO: 2) (line 7) and mutations present in the other probes (lines 1-6) relative to SEQ ID NO: 4.

| ID | Mutations |
|---|---|
| L1P8 H2 | Y14M L38M A72W |
| L2P22 G6 | M18I G31Y A73G |
| L10P7 A4 | Y14L M18L G31Y A73L Y117A |
| L11P7 B3 | M21F L78V L102V |
| L13P7 B4 | R106W Q115C |
| L18P5 G12 | Y14R M18L A72L A73F Y117D |
| ADIFAB2 | L72A |

TABLE 2

$FFA_u$ distributions determined in mixtures of 5 fatty acids with BSA.[a]

| | 1:1:1:1:1 | | | | 20:25:30:15:10 | | | | 25:20:33:19:3 | | | |
|---|---|---|---|---|---|---|---|---|---|---|---|---|
| | Experiment | | Model | | Experiment | | Model | | Experiment | | Model | |
| | $FFA_u$ (nM) | X (%) | $FFA_u$ (nM) | X (%) | $FFA_u$ (nM) | X (%) | $FFA_u$ (nM) | X (%) | $FFA_u$ (nM) | X (%) | $FFA_u$ (nM) | X (%) |
| AA | 0.200 | 22 | 0.191 | 21 | 0.170 | 19 | 0.191 | 21 | 0.259 | 27 | 0.249 | 26 |
| LA | 0.183 | 20 | 0.189 | 21 | 0.235 | 26 | 0.236 | 26 | 0.201 | 21 | 0.196 | 21 |
| OA | 0.106 | 12 | 0.175 | 19 | 0.230 | 25 | 0.262 | 29 | 0.254 | 27 | 0.299 | 32 |

TABLE 2-continued

FFA$_u$ distributions determined in mixtures of 5 fatty acids with BSA.[a]

| | 1:1:1:1:1 | | | | 20:25:30:15:10 | | | | 25:20:33:19:3 | | | |
|---|---|---|---|---|---|---|---|---|---|---|---|---|
| | Experiment | | Model | | Experiment | | Model | | Experiment | | Model | |
| | FFA$_u$ (nM) | X (%) | FFA$_u$ (nM) | X (%) | FFA$_u$ (nM) | X (%) | FFA$_u$ (nM) | X (%) | FFA$_u$ (nM) | X (%) | FFA$_u$ (nM) | X (%) |
| PA | 0.253 | 28 | 0.182 | 20 | 0.190 | 21 | 0.136 | 15 | 0.207 | 22 | 0.179 | 19 |
| SA | 0.164 | 18 | 0.170 | 19 | 0.085 | 9 | 0.085 | 9 | 0.028 | 3 | 0.026 | 3 |
| Total | 0.907 | | 0.907 | | 0.910 | | 0.910 | | 0.949 | | 0.949 | |
| AA | 0.727 | 23 | 0.737 | 23 | 0.776 | 24 | 0.748 | 23 | | | | |
| LA | 0.659 | 21 | 0.707 | 22 | 0.820 | 25 | 0.896 | 27 | | | | |
| OA | 0.622 | 20 | 0.573 | 18 | 0.930 | 28 | 0.868 | 27 | | | | |
| PA | 0.706 | 22 | 0.633 | 20 | 0.535 | 16 | 0.480 | 15 | | | | |
| SA | 0.464 | 15 | 0.531 | 17 | 0.203 | 6 | 0.268 | 8 | | | | |
| Total | 3.18 | | 3.18 | | 3.26 | | 3.26 | | | | | |
| AA | 6.22 | 32 | 5.63 | 29 | 5.52 | 29 | 5.39 | 28 | | | | |
| LA | 4.71 | 24 | 4.94 | 25 | 6.25 | 32 | 5.91 | 31 | | | | |
| OA | 2.51 | 13 | 2.89 | 15 | 3.76 | 20 | 4.16 | 22 | | | | |
| PA | 3.20 | 16 | 3.64 | 19 | 2.35 | 12 | 2.62 | 14 | | | | |
| SA | 2.93 | 15 | 2.46 | 13 | 1.37 | 7 | 1.18 | 6 | | | | |
| Total | 19.6 | | 19.6 | | 19.3 | | 19.3 | | | | | |

[a]Experimental FFA$_{ui}$ values were determined from three different mixtures (1:1:1:1:1, 20:25:30:15:10 and 25:20:33:19:3) of AA, LA, OA, PA and SA by analyzing the measured probe responses. The mixture ratios shown in the first line of the table indicate the relative volume ratios of the FFA:BSA complexes used to prepare the mixtures and these are roughly the final FFA$_{ui}$ ratios observed in the mixtures. Except for the 25:20:33:19:3 (0.9 nM), three concentrations of total FFA$_u$ (0.9, 3.2 and 20 nM) were used for each distribution. Model values of the FFA$_{ui}$ concentrations, where i designates a particular FFA in the mixture, were calculated using a single class binding model. Also shown is the fraction of each FFA$_{ui}$ in the mixture (X in %).

To our knowledge, no other method has been reported for determining the FFA$_u$ distribution in a mixture of FFA. Although methods exist to measure the distribution of total (albumin bound and unbound) FFA, this profile differs considerably from the FFA$_u$ profile because of differences in FFA-BSA binding affinities. This difference is illustrated in Table 3 where the measured and model-predicted FFA$_u$ distributions are shown with the predicted and experimentally determined total FFA distributions for two of the mixtures of Table 2. These results reveal, for example, that similar FFA$_u$ values for SA and AA can only be achieved when the total SA concentration is substantially higher than the total AA concentration, as expected from the difference in SA and AA binding affinities.

TABLE 3

FFA$_u$ and total FFA distributions of two mixtures of 5 fatty acids with BSA.[a]

| | 1:1:1:1:1 | | | | | | | | 20:25:30:15:10 | | | | | | | |
|---|---|---|---|---|---|---|---|---|---|---|---|---|---|---|---|---|
| | Experiment | | | | Model | | | | Experiment | | | | Model | | | |
| | FFA$_u$ (nM) | X % | Total FFA (μM) | X % | FFA$_u$ (nM) | X % | Total FFA (μM) | X % | FFA$_u$ (nM) | X % | Total FFA (μM) | X % | FFA$_u$ (nM) | X % | Total FFA (μM) | X % |
| AA | 0.73 | 23 | 115 | 10 | 0.74 | 23 | 122 | 11 | 0.78 | 24 | 115 | 11 | 0.75 | 23 | 124 | 11 |
| LA | 0.66 | 21 | 169 | 15 | 0.71 | 22 | 171 | 15 | 0.82 | 25 | 212 | 20 | 0.90 | 27 | 217 | 20 |
| OA | 0.62 | 20 | 267 | 24 | 0.57 | 18 | 262 | 24 | 0.93 | 28 | 400 | 37 | 0.87 | 27 | 406 | 38 |
| PA | 0.71 | 22 | 240 | 21 | 0.63 | 20 | 219 | 20 | 0.54 | 16 | 180 | 17 | 0.48 | 15 | 167 | 15 |
| SA | 0.46 | 15 | 330 | 29 | 0.53 | 17 | 331 | 30 | 0.20 | 6 | 165 | 15 | 0.27 | 8 | 168 | 15 |
| Total | 3.2 | | 1121 | | 3.2 | | 1108 | | 3.3 | | 1072 | | 3.3 | | 1082 | |

[a]Experimental values of the total FFA profiles were determined from the amount of FFA that was used to make each FFA:BSA complex. The mixture ratios shown in the first line of the table indicate the relative volume ratios of the FFA:BSA complexes used to prepare the mixtures and these are roughly the FFA$_{ui}$ ratios observed in the mixtures. (Note that the total FFA concentrations are the concentrations before the mixtures were diluted 100 fold in Measurement Buffer.) Model values of the total FFA profiles were calculated from the single class BSA binding model.

In addition to its greater physiologic relevance, the determination of the $FFA_u$ profile has a number of important advantages over the total distribution methods, especially for biologic fluids such as blood plasma. $FFA_u$ profiling using the fluorescent probes, for example in blood plasma, requires little sample preparation. In contrast, measuring the total FFA distribution requires extensive procedures to extract and separate the lipid components using organic solvents that can themselves alter the FFA distribution. Probe-based measurements require less sample because the measurements are performed directly in 100-fold diluted plasma (Richieri, G. V., et al. (1995) Unbound free fatty acid levels in human serum, *J. Lipid Res.* 36, 229-240; Richieri, G. V., et al. (1999) The measurement of free fatty acid concentration with the fluorescent probe ADIFAB: A practical guide for the use of the ADIFAB probe, *Mol. Cell. Biochem.* 192, 87-94) and the measurements are amenable to high throughput techniques such as fluorescent scanning in multi-well plates. On the other hand, probe specificity must be carefully investigated to account for potential interferents in biologic fluids.

Example 2

Using Multiple Probes to Help Diagnose ST-Elevation Myocardial Infarction

Early detection of coronary dysfunction is often not possible. For example, the ECG which is the primary early diagnostic tool for acute coronary syndromes is less than 50% sensitive. Thus a sensitive, accurate and rapid test for ischemia is needed for the diagnosis and treatment of patients.

The magnitude of the sum of the different FFAu in blood (total FFAu—measured with a single probe) increases in patients with cardiac ischemia (see U.S. Pat. No. 6,750,030 which is incorporated herein by reference). The single-probe measurements of FFAu in these previous studies were carried out with ADIFAB or ADIFAB2 and the observed increase in total FFAu was shown to be diagnostic of cardiac ischemia.

In order to see whether metabolic profiling could provide a diagnostic measurement with greater sensitivity and selectivity, blood samples from the TIMI II trial (blood repository of the National Heart Lung Blood Institute of the NIH) and 146 healthy volunteers (normals) were used to determine if changes in the profile of different metabolites is significantly different in patients with cardiac ischemia as compared to individuals without cardiac ischemia. The ischemic blood samples were from 250 TIMI II trial enrolled patients with ST segment myocardial infarction who presented to the emergency department within 4 hours of symptom. Patient samples were collected upon arrival in the emergency department. All samples were measured with ADIFAB2 and with 6 additional probes (Table 1). FFAu levels measured with ADIFAB2 were elevated in TIMI II patients compared to normals with a sensitivity of 71% (using the normals 95% cutoff). However measurements of the sample response profiles of the same samples with the 7 probes of Table 1 yielded an improved 83% sensitivity by discriminant analysis (FIG. 1). These results indicate that there are metabolic profile differences, most likely FFAu profile differences that are significantly different in normals and MI patients.

Example 3

Analysis Using Bayesian Decision Theory

Blood samples from 146 healthy controls and 447 TIMI II patients were measured with ADIFAB2 and 6 additional probes (Table 1) as described in Example 2.

Table 4 shows the results using a classifier to separate these 2 groups derived from two-group Bayesian decision theory using the sample response profiles $\{\Delta Ro^k/Ro^k\}$s for each of these 7 probes.

TABLE 4

Percentage of samples classified correctly using Bayesian decision theory with 7 probes. All calculations were performed with XLSTAT, an Excel add-in for statistical analysis.

| Group | Healthy Group (Specificity) | MI (Sensitivity) |
|---|---|---|
| Training Set | 83.1% | 90.4% |
| Testing Set | 85.7% | 91.7% |

Table 5 shows the specificity and sensitivity for each of the 7 probes of Table 1 used alone to analyze the blood specimens from the same individuals used for the results shown in Table 4. These results demonstrate that using multiple probes greatly improves the accuracy of detecting cardiac ischemia relative to any of the seven probes used alone.

TABLE 5

Specificity and sensitivity of each probe.

| Probe | Healthy Group (Specificity) | MI Group (Sensitivity) |
|---|---|---|
| L1P8 H2 | 83.6% | 77.5% |
| L2P22 G6 | 95.9% | 71.6% |
| L11P7 B3 | 89.0% | 79.4% |
| L13P7 B4 | 94.5% | 64.7% |
| L10P7 A4 | 93.8% | 72.5% |
| L18P5 G12 | 92.5% | 72.9% |
| ADIFAB2 | 93.8% | 72.5% |

Example 4

Using a Probe for UCBf for Titration of UCBf in Adult Samples

Adult Plasma—

Investigations of the effects of FFA on our UCB probes are necessary because the probes are constructed from FABP mutants and FFA are abundant in plasma. Interference testing of every possible component of plasma, however, is not feasible. Therefore $UCB_f$ was measured in samples of diluted plasma, from 6 healthy adult donors, titrated with UCB. Because the $[UCB_f]$ is determined by the UCB:HSA ratio, the [HSA] of each plasma sample was measured using a Bromcresol Green Albumin Determination Kit from Sigma-Aldrich. HSA concentrations were similar for all samples and ranged from 620 to 680 μM. Plasma $[FFA_u]$ was measured with ADIFAB2 and ranged from 1.0 to 3.6 nM. The L24P19C7 probe at 0.5 μM was used to measure $[UCB_f]$ in 1% plasma (i.e., 6.2 to 6.8 μM HSA) titrated with UCB (FIG. 2). This probe has the following mutations with reference to rat Intestinal Fatty Acid Binding Protein (SEQ ID NO: 4): Y14R M18L L38V V60R A72L A73F R106C Q115R and Y117D. Without the addition of UCB, all samples yielded a $[UCB_f]$ of nearly zero, in good agreement with the 0 to 1 nM $[UCB_f]$ expected for a healthy adult. This result suggests that adult plasma is free of interference that would inflate probe-based $[UCB_f]$ estimates. In addition, all samples showed a monotonic increase in $[UCB_f]$ with the addition of UCB, strongly suggesting that the probe correctly responds to $UCB_f$ in plasma. Indeed, the increase was consistent with the change in [UCB$_f$] predicted using the equilibrium-binding model, confirming the accuracy of the probe in plasma.

Example 5

Using a Probe for UCBf for Detection of Hyperbilirubinemia in Neonates

Figure 3:
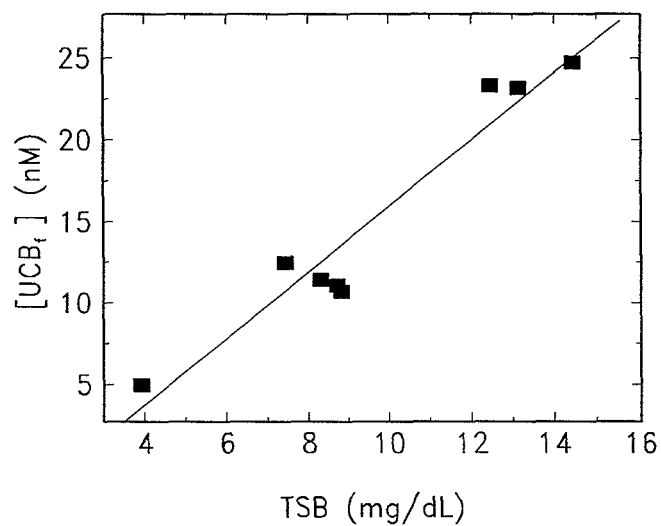
FIG. 3 shows correlation between free/unbound unconjugated bilirubin (UCB$_f$) and total serum bilirubin (TSB) for neonatal plasma. A strong correlation (R=0.966, p<0.0001) is observed for the UCB$_f$ and TSB data (squares) as revealed by the linear fit (line).

Plasma samples from 8 jaundiced neonates were tested. Blood samples were collected via heel stick and centrifuged to obtain plasma for clinical total serum bilirubin (TSB) measurements. Plasma from these blood samples was frozen at −80° C. and later used for UCB$_f$ measurements. Duplicate measurements of 100-fold dilutions of 15 µL plasma were performed for each sample using 0.5 µM of the L24P19C7 probe. Comparison of these UCB$_f$ measurements with the clinically determined TSB values reveals an excellent correlation (R=0.966, p<0.0001) between the two measurements (FIG. 3). These results are consistent with the UCB-spiked adult plasma experiments and show that L24P19C7 can accurately measure [UCB$_f$] in neonatal plasma.

Example 6

Use of Multiple Probes to Diagnose Non Alcoholic Fatty Liver Disease and Diabetes Non alcoholic fatty liver disease (NAFLD) is an increasingly important medical problem because of the rapidly increasing population of overweight and obese individuals. Estimates place the frequency of NAFLD occurrence at 20% of obese individuals and it's estimated that 30% of the US population is obese. Patients with NAFLD can progress from simple steatosis to end stage cirrhosis. However, diagnosing the early stage is difficult because there are often no symptoms and confirmation of the disease requires a liver biopsy. Therefore a non-invasive and inexpensive means of accurately diagnosing NAFLD is an important unmet medical problem.

In this example we have determined the sample response profiles $\{\Delta R^k/Ro^k\}$s of the 7 different probes of Table 1 to determine if unbound free fatty acid (FFA) metabolomics could be used to distinguish metabolic profiles of Non-Alcoholic Steatohepatitis (NASH) patients from healthy controls and patients with diabetes. Distinguishing NAFLD and diabetes is important because most NAFLD patients also suffer from type 2 diabetes.

For this example we compared the response of 7 probes in blood samples from the 146 normals of example 2, with samples from 38 patients with NAFLD confirmed by biopsy and 48 patients suffering from type 2 diabetes. The response of the 7 probes yields a sample response profile for each sample. We used the discriminant analysis (DA) method of example 3, using the logarithm of the sample response profiles $\{\Delta R^k/Ro^k\}$s to distinguish the 3 different physiologic states.

Figure 4:
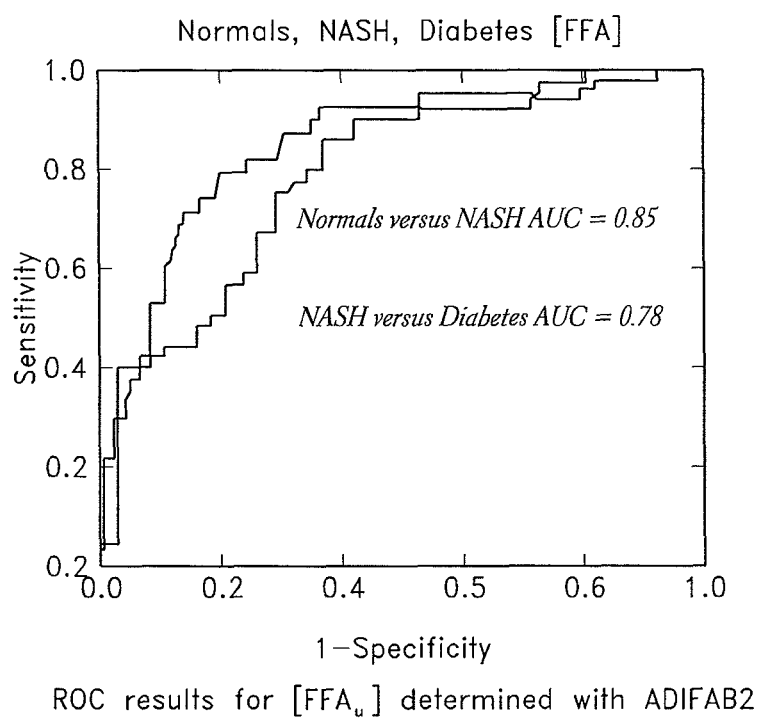
FIG. 4 shows receiver operator curve (ROC) results for [FFA$_u$] determined with ADIFAB2.

First, total FFA$_u$ levels were measured in all samples using ADIFAB2 as described (Richieri, G V, Kleinfeld, A M: Unbound free fatty acid levels in human serum. *J Lipid Res* 36:229-240, 1995; Apple, F S, et al.: Unbound Free Fatty Acid Concentrations Are Increased in Cardiac Ischemia. *Clinical Proteomics* 1:41-44, 2004; U.S. Pat. Nos. 6,444,432 & 6,750,030, all incorporated by reference). The results yielded total [FFA$_u$] averages and standard deviations for the normals, NASH and diabetes patients. The values were found to be 1.4±0.6 nM for normals, 2.5±1.1 nM for NASH and 3.7±1.5 nM for diabetes. The increase in NAFLD and diabetes is consistent with previous reports of increases in total FFA. Discriminant analysis was applied to these results and the receiver operator curve (ROC) for normals versus NASH and NASH versus diabetes are shown in FIG. 4. The area under the curve (AUC) was 0.85 and for NASH versus diabetes it was 0.78. For normals versus NASH this AUC yields sensitivities and specificities of about 80% each while for NASH versus diabetes an 80% sensitivity corresponds, approximately, to a 70% specificity.

Figure 5:
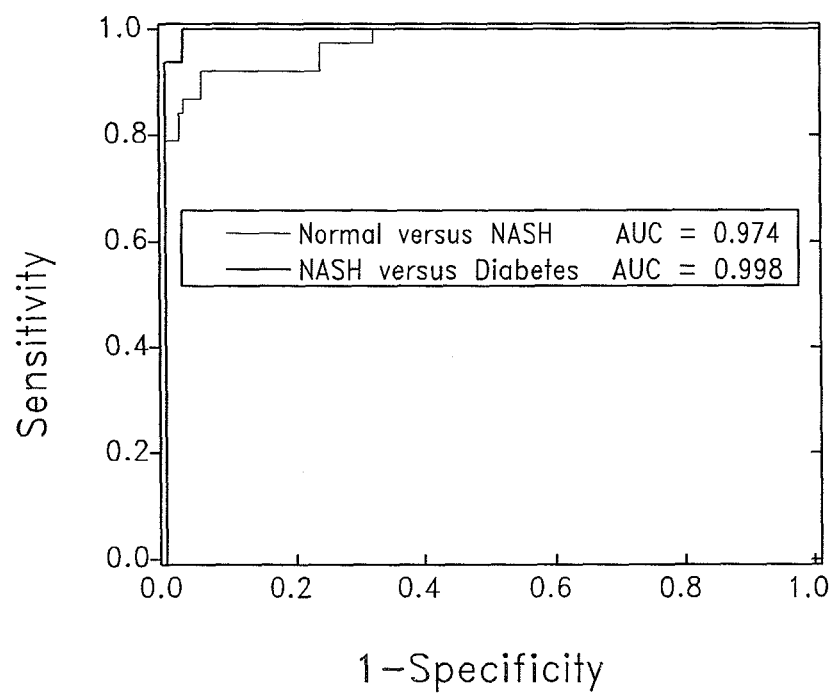
FIG. 5 shows ROCs from 7 probe discriminant analysis.

In a separate experiment, measurements of the response of 7 different probes (Table 1), transformed as ln(ΔR/Ro), were the inputs used for discriminant analysis. The multi-probe discriminant analysis results for normals versus NASH and NASH versus diabetes yielded AUCs for their respective ROCs of 0.974 and 0.998 (FIG. 5). These ROCs correspond to sensitivities and specificities of 92% and 89% for normals versus NASH and 96% and 97% for NASH versus diabetes.

Figure 6:
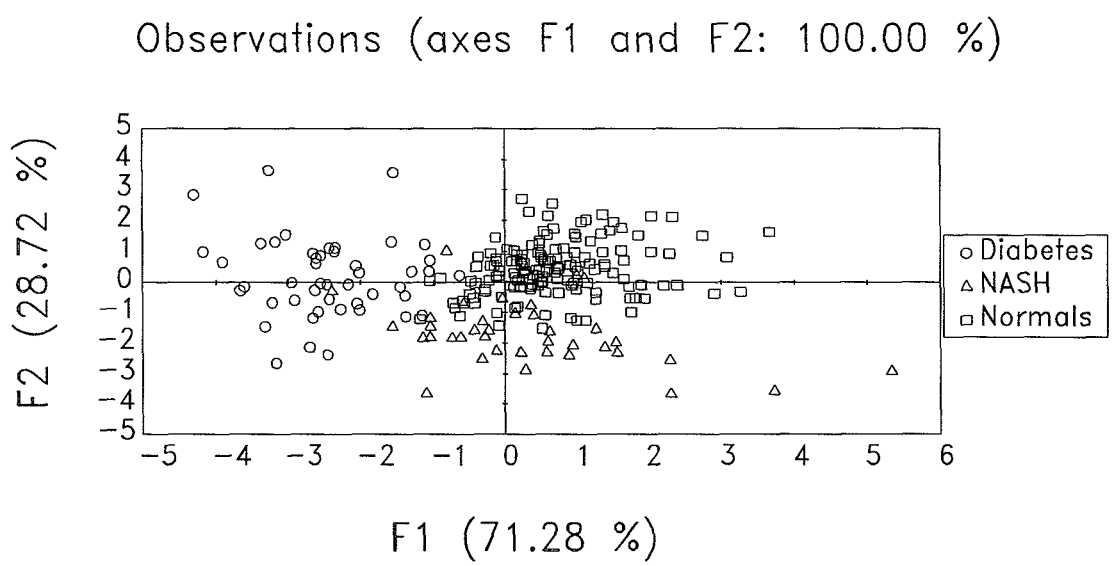
FIG. 6 shows three group discriminant analysis of Normals, Non-Alcoholic Steatohepatitis (NASH) and diabetics.

In addition to these 2 group discriminant analyses we performed discriminant analysis for the 3 groups: normals, NASH and diabetes. The results indicate that discriminant analysis is capable of separating all 3 groups (FIG. 6). These results indicate that the sample response profiles and FFA$_u$ profiles are highly accurate indicators of NAFLD and diabetes.

Example 7

Multiple Probes Help Distinguish Acute Coronary Syndrome (ACS) and Other Diseases that Elevate FFA Level Differences in the sample response profiles in blood specimens of healthy individuals, subjects with non-ACS diseases, and patients suffering from ACS were compared. The source and number of samples within each subject group are given in Table 6. All samples were measured using the seven different probes of Table 5.

TABLE 6

Description and number of samples from each subject group.

| Sample Group | Group Size |
| --- | --- |
| Healthy | 226 |
| All Non-ACS Diseases includes the following | 208 |
| Non-alcoholic fatty liver disease | 38 |
| Type II Diabetes | 48 |
| Stroke | 67 |
| Sepsis | 55 |
| ACS | 416 |

In this example we used the following nonlinear quantity to define the probe response in each sample as $(R-R_o)/(R_{max}-R)$, where R is the fluorescence ratio ($I_{550}/I_{457}$) in plasma, $R_o$ is the ratio with no fatty acids present, and $R_{max}$ is the ratio when the probe is saturated with FFA. Sample response profiles $\{(R^k-R^k_o)/(R^k_{max}-R^k)\}$ were obtained by measuring each plasma sample with each of the seven probes. Differences between the sample profiles in control and TIMI groups were exploited to design a classifier that distinguished between all non-ACS (healthy and disease) and ACS populations. Two-group (non-ACS and TIMI patients) Bayesian decision theory was used to construct this classifier (Duda R O, Hart P E and Stork D G. *Pattern Classification*. John Wiley & Sons, Inc., 2001). The class-conditional probability for the two groups was calculated using the distribution of response profiles within the two populations. Samples from both groups were set aside to construct the classifier, and the rest of the samples were tested once the optimum classifier was found.

In this analysis 400 samples (204 controls and 196 MI patients) of the 850 total samples were randomly set aside as a test set and the remaining 450 (230 non-ACS and 220 MI patients) were used as the training set to calculate the class-conditional probability density functions. Approximately 90% of samples in each group were classified correctly (specificity and sensitivity) using the derived classification functions and the results were similar for the training and testing sets (Table 7). Comparable results were obtained with other testing sets chosen randomly from the same total sample pool. This demonstrates that the classification functions are robust across different data sets.

TABLE 7

Percentage of samples classified correctly using Bayesian decision theory with 7 probes. All calculations were performed with XLSTAT, an Excel add-in for statistical analysis.

| Group | Non-ACS (Specificity) | MI (Sensitivity) |
|---|---|---|
| Training Set | 87.0% | 90.9% |
| Testing Set | 88.7% | 90.8% |

Figure 7:
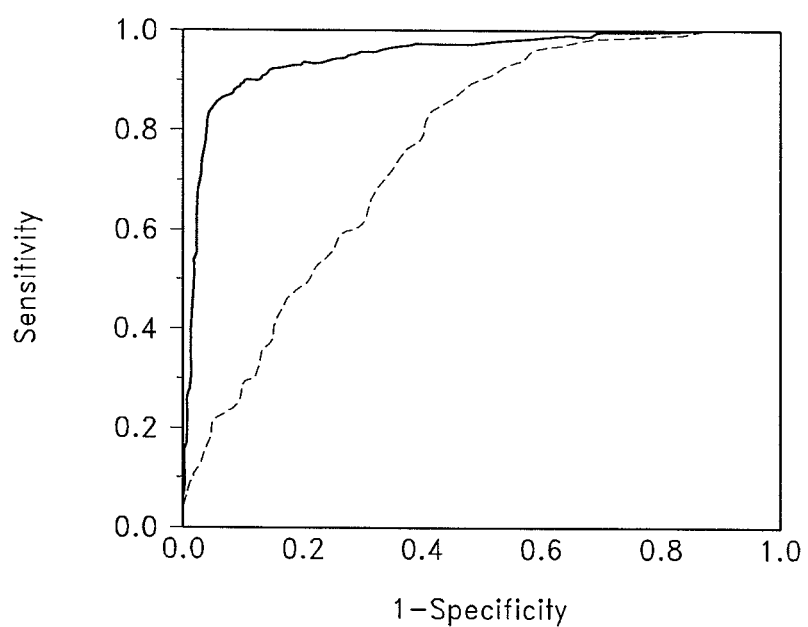
FIG. 7 shows ROC curves that show that multiple probes improve performance. Sensitivity and specificity data were generated from TIMI and non-ACS populations. Compared to ADIFAB2, the use of 7 probes improves sensitivity and specificity, and increases the AUC from 0.76 to 0.95.

In addition to the single specificity and sensitivity values, we also generated receiver operating characteristic (ROC) curves for the Bayesian 7 probe analysis and each individual probe. The ROC curves show the entire range of sensitivity and specificity values, and the area under the ROC curve (AUC) provides a single value measure of the overall diagnostic performance of a test. As can be seen from FIG. 7, the Bayesian classifier derived from the 7 probe analysis performs much better than the single ADIFAB2 probe, with substantially better sensitivity at high specificity (low [1−specificity]). Moreover, the 7 probe Bayesian classifier significantly outperforms all individual probes as reflected in the AUC values, which range from 0.72 to 0.82 for the single probes as compared to 0.95 for the multiple probe method.

ACS is considered a spectrum of diseases ranging from unstable angina to non-ST-segment elevation MI (NSTEMI) to ST-segment elevation MI (STEMI), the most severe form of ACS. We investigated whether our probe measurements are consistent with a continuum of severity. The sample response profiles from the non-ACS and TIMI II samples were used to generate a Fisher linear discriminant function (Duda R O, Hart P E and Stork D G. *Pattern Classification*. John Wiley & Sons, Inc., 2001). Based on the continuous values of the Fisher discriminant function, a sample can be identified as being from an MI or non-ACS patient. The discriminant function generated from the TIMI II population, which is comprised only of STEMI patients, can be used to predict the diagnosis of EARLY patients, which were unstable angina and NSTEMI only.

Figure 8:
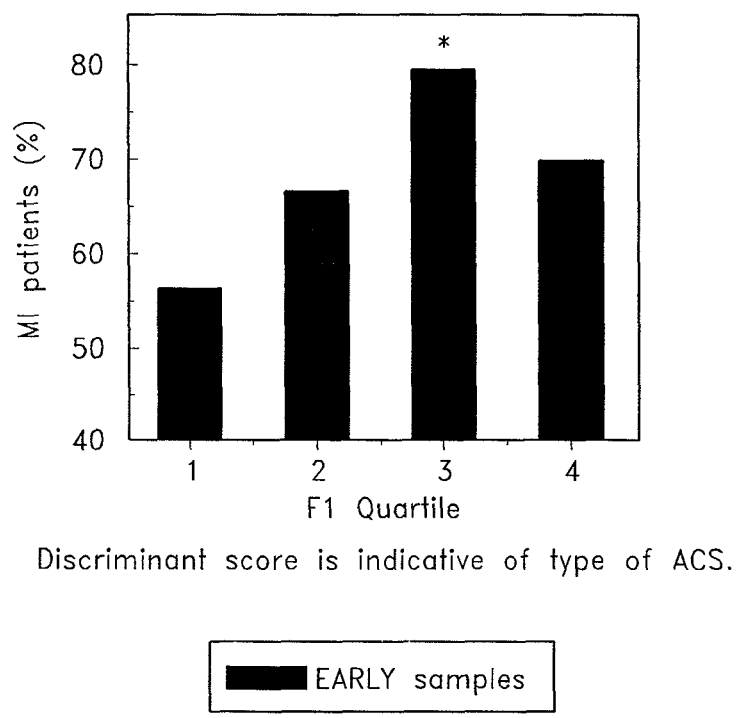
FIG. 8 shows that discriminant score is indicative of type of ACS. EARLY samples were measured with 7 probes and divided into quartiles with mean F1 scores of −0.81 (1), 0.26 (2), 0.71 (3), and 1.50 (4). The percent of MI patients (remainder are unstable angina) in each quartile is shown. The third quartile (*) is significantly (p=0.002) different from the first quartile by logistic regression.

We measured 309 baseline EARLY samples with the same 7 probes used to generate the non-ACS versus TIMI II Fisher discriminant function and, using that function, calculated the discriminant score (F1) for each EARLY sample. The samples were then divided into quartiles based on the discriminant score. As shown in FIG. 8, quartile 1 (mean F1=−0.81) had the fewest MI patients (56%) and quartile 3 (mean F1=0.71) had the most (79%). The difference was statistically significant (p=0.002) by logistic regression. Interestingly, the F1 values for quartiles 1 and 3 are closest to the mean F1 values for the non-ACS (−0.81) and TIMI II (0.85) populations, respectively. The results of FIG. 8 indicate that the discriminant function derived from the non-ACS and TIMI II populations can be used to 1) identify any type of MI patient and 2) stratify patients for likelihood of MI versus unstable angina (reversible ischemia). Furthermore, the applicability of the TIMI II derived discriminant function to other types of ACS patients implies that cardiac ischemia in general has a specific metabolic signature that can be detected with our $FFA_u$ probes.

Figure 9:
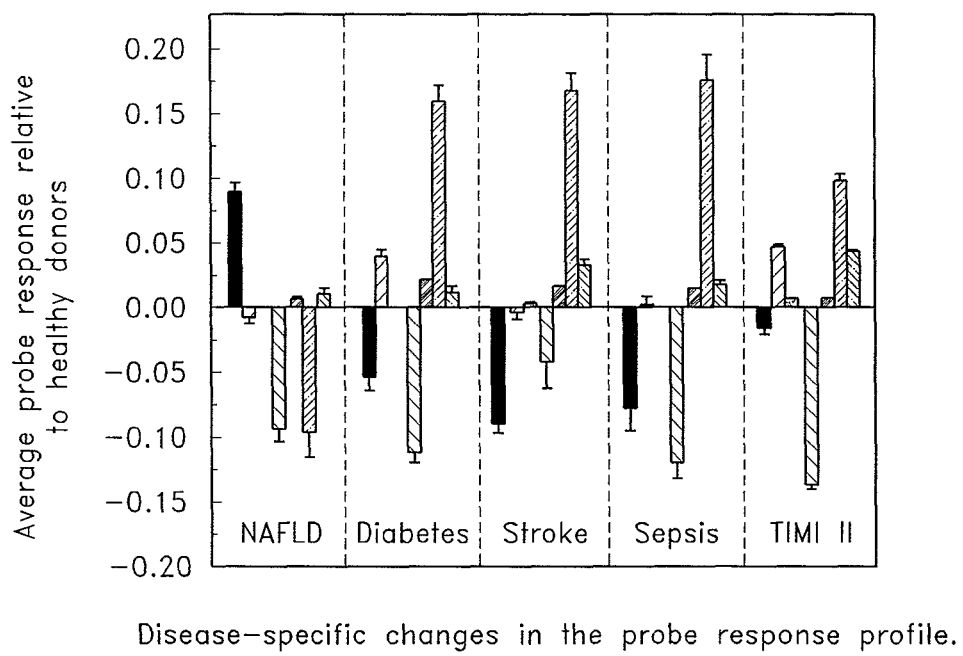
FIG. 9 shows disease-specific changes in the probe response profile. Average normalized probe responses were determined for Non-Alcoholic fatty liver disease (NAFLD), Diabetes, Stroke, Sepsis and Cardiac diseases and healthy subjects.
Figure 9:
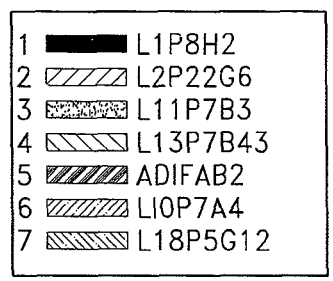

The classification results indicate that the pattern of probe responses for plasma from MI patients differs from the response pattern for plasma from non-ACS subjects. To illustrate this difference, a normalized probe response profile was calculated for each sample from Table 2. Each probe response was normalized by dividing by the square root of the sum of each squared response. From these values, the mean profile for each disease was determined and subtracted the mean healthy profile from each disease profile. The resulting profile differences indicate the change in relative response of each probe from a healthy to a given disease state (FIG. 9). For example, the relative response from L10P7A4 is less for non-alcoholic fatty liver disease (NAFLD) than for healthy donors, but it is greater for all other diseases. Multivariate analysis of variance indicates that all diseases are statistically different from healthy donors and each other (p<0.05), suggesting that each disease has a specific $FFA_u$ profile signature.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of determining a sample probe response profile of two or more probes of unbound free fatty acids (FFAu) in body fluids for a test individual comprising:
   measuring a fluorescence index for the two or more probes of FFAu wherein the fluorescence index comprises fluorescence intensity, ratio of intensities at two excitation and/or emission wavelengths, polarization and/or lifetime for the two or more probes, and wherein each of the two or more probes comprise a mutant intracellular lipid binding protein labeled with a fluorophore, and wherein the two or more probes each have different specificities for different FFAu and generate a change in fluorescence index upon binding FFAu;
   obtaining a body fluid sample from the test individual;
   contacting the body fluid sample with the two or more probes of FFAu;
   measuring a sample response for each of the two or more probes in the body fluid sample to generate the sample probe response profile, wherein measuring the sample response comprises measuring the change in the fluorescence index as a result of contact with the body fluid sample with each of the two or more probes; and
   applying a statistical classification analysis to determine the probability that the sample response profile corresponds to a state different from a state of a preselected control population.

2. The method of claim 1, wherein the preselected control population comprises individuals without disease symptoms and the test individual is a patient presenting with symptoms of the disease.

3. The method of claim 1, wherein the preselected control population comprises individuals who have not been treated with a test drug and the test individual is an individual who has been treated with the test drug.

4. The method of claim 1, wherein the preselected control population comprises individuals who have not been administered with test nutrients and the test individual is an individual who has been administered with test nutrients.

5. The method of claim 1, wherein the body fluid is selected from the group consisting of whole blood, blood plasma, blood serum, urine, CSF, saliva, gastric juices, bile, amniotic fluid, breast milk, seminal fluid, interstitial fluid, synovial fluid, plant sap and lymph.

6. The method of claim 1, wherein the statistical classification analysis is a mathematical method for classifying results into distinct groups, which is used to determine the probability that the response profile corresponds to the state of the preselected control population.

7. The method of claim 6, wherein the statistical classification analysis method is principal component analysis, discriminant analysis, decision trees, k-nearest neighbors, logistic regression, support vector machines, classification analysis based on Bayesian decision theory, analysis based on artificial neural networks techniques or a mathematical method for pattern recognition or classifying metabolomic results.

8. The method of claim 1, wherein the proteins are fatty acid binding protein muteins.

9. The method of claim 1, wherein the proteins are intestinal fatty acid binding protein muteins.

10. The method of claim 1, wherein the fluorophore is acrylodan.

11. The method of claim 9, wherein the fatty acid binding protein muteins are selected from ADIFAB2 (L72A mutein relative to SEQ ID NO: 2) and fatty acid binding protein muteins comprising mutations in at least two positions selected from the group consisting of 14, 18, 21, 31, 38, 72, 73, 78, 102, 106, 115, and 117 relative to the L72A mutein of the rat Intestinal-FABP shown as SEQ ID NO: 2.

12. The method of claim 1, wherein the two or more probes comprise at least two selected from L1P8H2, L2P22G6, L10P7A4, L11P7B3, L13P7B4, L18P5G12 and ADIFAB2.

13. The method of claim 1, further comprising analyzing the fluorescence indices by pattern classification or discriminant analysis methods to obtain a diagnosis.

14. The method of claim 1, wherein the sample response for each of the one or more probes is calculated as $\Delta R/Ro$, or the logarithm of $\Delta R/Ro$ and wherein R is the fluorescence emission ratio ($I_{550}/I_{457}$) in plasma, $R_o$ is the fluorescence ratio of the probe with no fatty acids present, and $\Delta R$ is the difference between R and Ro.

15. The method of claim 1, wherein the sample response for each of the one or more probes is calculated as $\Delta R/(Rmax-R)$, or the logarithm of $\Delta R/(Rmax-R)$ and wherein R is the fluorescence emission ratio ($I_{550}/I_{457}$) in plasma, $\Delta R$ is the difference between R and Ro, $R_o$ is the fluorescence ratio of the probe with no fatty acids present, and Rmax is the fluorescence ratio ($I_{550}/I_{457}$) of the probe when the probe is saturated with FFA.

16. The method of claim 14, further comprising analyzing the fluorescence indices by pattern classification or discriminant analysis methods to obtain a diagnosis.

17. The method of claim 15, further comprising analyzing the fluorescence indices by pattern classification or discriminant analysis to obtain a diagnosis.

18. The method of claim 1, wherein the body fluid sample is from a patient with symptoms of cardiac dysfunction, non-alcoholic fatty liver disease (NAFLD), stroke, sepsis or diabetes and the preselected control population is one or more individuals without symptoms of cardiac dysfunction, non-alcoholic fatty liver disease (NAFLD), stroke, sepsis or diabetes.

19. A method of screening a patient for cardiac dysfunction, non-alcoholic fatty liver disease (NAFLD), stroke, sepsis or diabetes comprising:
   measuring a fluorescence index of at least two probes selected from the group consisting of L1P8H2, L2P22G6, L10P7A4, L11P7B3, L13P7B4, L18P5G12 and ADIFAB2, wherein each of the probes comprise a mutant intracellular lipid binding protein labeled with a fluorophore, wherein each of the probes has different specificities for different FFAu and generate a change fluorescence index upon binding and wherein the fluorescence index comprises fluorescence intensity, ratio of intensities at two excitation and/or emission wavelengths, polarization and/or lifetime of the probes;
   withdrawing a fluid sample from the patient;
   contacting the fluid sample with said at least two probes;
   measuring the change in fluorescence index of the probes as a result of contact with the fluid sample;
   determining the probe response profile in the fluid sample from the measured change in probe fluorescence index for each of the probes;
   comparing the probe response profile in the sample to the probe response profile in a normal population, without symptoms of cardiac dysfunction, non-alcoholic fatty liver disease (NAFLD), stroke, sepsis or diabetes using statistical classification analysis; and
   correlating the probe response profile with the presence or absence of cardiac dysfunction, non-alcoholic fatty liver disease (NAFLD), stroke, sepsis or diabetes in the patient.

20. The method of claim 19, wherein the cardiac dysfunction is acute coronary syndrome.

* * * * *